United States Patent
Schneider

(10) Patent No.: US 9,636,263 B2
(45) Date of Patent: May 2, 2017

(54) METHODS AND APPARATUS FOR ASSEMBLING REFASTENABLE ABSORBENT ARTICLES

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 471 days.

(21) Appl. No.: 14/201,992

(22) Filed: Mar. 10, 2014

(65) Prior Publication Data

US 2014/0274646 A1  Sep. 18, 2014

Related U.S. Application Data

(60) Provisional application No. 61/786,871, filed on Mar. 15, 2013.

(51) Int. Cl.
| | |
|---|---|
| *A61F 13/15* | (2006.01) |
| *A61F 13/49* | (2006.01) |
| *A61F 13/56* | (2006.01) |
| *A61F 13/496* | (2006.01) |

(52) U.S. Cl.
CPC .. *A61F 13/15804* (2013.01); *A61F 13/15756* (2013.01); *A61F 13/15764* (2013.01); *A61F 13/49011* (2013.01); *A61F 13/49061* (2013.01); *A61F 13/4963* (2013.01); *A61F 13/565* (2013.01); *A61F 13/15699* (2013.01); *A61F 13/15747* (2013.01); *A61F 13/496* (2013.01); *A61F 2013/15878* (2013.01); *A61F 2013/49026* (2013.01)

(58) Field of Classification Search
None
See application file for complete search history.

(56) References Cited

U.S. PATENT DOCUMENTS

| | | | |
|---|---|---|---|
| 3,848,594 A | 11/1974 | Buell | |
| 4,662,875 A | 5/1987 | Hirotsu et al. | |
| 4,846,815 A | 7/1989 | Scripps | |

(Continued)

OTHER PUBLICATIONS

PCT International Search Report dated Sep. 11. 2014, 9 pages.

*Primary Examiner* — Barbara J Musser
(74) *Attorney, Agent, or Firm* — Sarah M. DeCristofaro; Abbey A. Lopez

(57) ABSTRACT

A method for assembling pre-fastened refastenable absorbent articles includes advancing discrete chassis in a machine direction such that the lateral axis is parallel with the machine direction. The chassis defines a first waist region and a longitudinally opposed second waist region separated by a central region. A first web advances in the machine direction and is combined with a discrete fastener component having a refastenable element. The discrete chassis are combined with the first web in the first waist region of the chassis. The second waist region of the discrete chassis is combined with a second web advancing in the machine direction. The chassis are folded and the first and second webs are joined together. The discrete fastener component is permanently connected with the second web. The absorbent article is cut along the discrete fastener component to create discrete, pre-fastened refastenable absorbent articles.

15 Claims, 21 Drawing Sheets

(56) References Cited

U.S. PATENT DOCUMENTS

| | | | |
|---|---|---|---|
| 4,894,060 A | 1/1990 | Nestegard | |
| 4,946,527 A | 8/1990 | Battrell | |
| 5,151,092 A | 9/1992 | Buell et al. | |
| 5,221,274 A | 6/1993 | Buell et al. | |
| 5,702,551 A | 12/1997 | Huber et al. | |
| 6,251,097 B1 | 6/2001 | Kline et al. | |
| 6,432,098 B1 | 8/2002 | Kline et al. | |
| 6,450,321 B1 | 9/2002 | Blumenthal et al. | |
| 6,669,618 B2 | 12/2003 | Reising et al. | |
| 7,201,744 B2 | 4/2007 | Van Gompel et al. | |
| 7,569,039 B2 | 8/2009 | Matsuda et al. | |
| 8,029,634 B2 * | 10/2011 | Widlund | A61F 13/565 156/204 |
| 8,607,959 B2 | 12/2013 | Papsdorf et al. | |
| 2003/0047273 A1 * | 3/2003 | Kojo | A61F 13/15609 156/250 |
| 2003/0135184 A1 | 7/2003 | Van Gompel et al. | |
| 2005/0107764 A1 | 5/2005 | Matsuda et al. | |
| 2007/0078427 A1 | 4/2007 | Raycheck et al. | |
| 2007/0093769 A1 | 4/2007 | Kline et al. | |
| 2007/0219521 A1 | 9/2007 | Hird et al. | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |
| 2012/0021186 A1 | 1/2012 | Schneider | |
| 2012/0061015 A1 | 3/2012 | LaVon et al. | |
| 2012/0061016 A1 | 3/2012 | LaVon et al. | |
| 2012/0152447 A1 | 6/2012 | Schneider | |
| 2012/0178609 A1 * | 7/2012 | Yamamoto | B65H 37/06 493/454 |
| 2013/0213547 A1 | 8/2013 | Schneider et al. | |
| 2013/0218116 A1 | 8/2013 | Schneider et al. | |
| 2013/0270065 A1 | 10/2013 | Papsdorf et al. | |
| 2013/0270066 A1 | 10/2013 | Papsdorf et al. | |
| 2013/0270067 A1 | 10/2013 | Papsdorf et al. | |

* cited by examiner

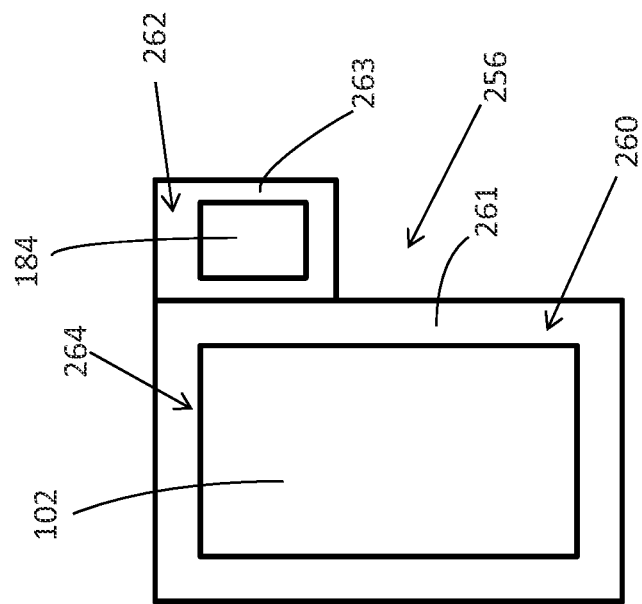
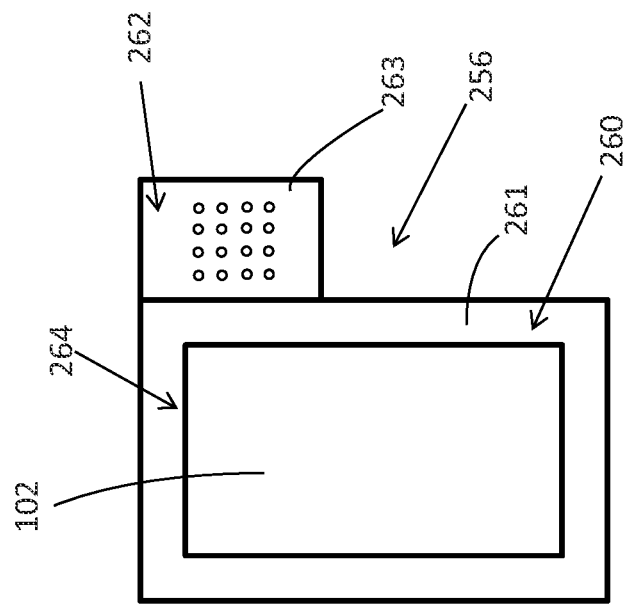

METHODS AND APPARATUS FOR ASSEMBLING REFASTENABLE ABSORBENT ARTICLES

FIELD OF THE INVENTION

The present disclosure relates to methods and apparatuses for assembling disposable absorbent articles, and more particularly, to methods and apparatuses for assembling pre-fastened refastenable disposable absorbent articles.

BACKGROUND OF THE INVENTION

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete diapers or other absorbent articles.

In some converting configurations, discrete chassis spaced apart from each other are advanced in a machine direction and are arranged with a longitudinal axis parallel with the cross direction. Opposing waist regions of discrete chassis are then connected with continuous lengths of elastically extendable front and back belts advancing in the machine direction to form a continuous length of absorbent articles. In some processes, the continuous length of absorbent articles advances in the machine direction with a topsheet of the discrete chassis facing down, toward the converting equipment. As such, the inner, wearer facing surfaces of the chassis and front and back belts may remain free of contamination caused during the assembly process by materials such as adhesive falling onto the advancing absorbent articles.

In some processes, it may be desirable for the front and/or back waist belts to be refastenable from each other, or from the discrete chassis. Some processes may combine discrete fastener components with the front waist belt during the converting process prior to folding the chassis. Sometimes, adhesive may be used to attach the discrete fastener components with the first and second waist belts. However, in a converting configuration where the inner, wearer facing surface is down, toward the converting apparatus, the adhesive on the discrete fastener components may cause the discrete fastener components to get stuck on the converting apparatus. Moreover, the discrete fastener components may advance through the assembly process uncontrollably until the discrete chassis is folded and the first and second waist belts are brought together, which may cause the discrete fastener components to bunch or disassemble.

Therefore, it would be beneficial to provide a method and apparatus for controlling the discrete fastener component prior to folding the discrete chassis. Additionally, it would be beneficial to provide a method and apparatus for forming pre-fastened refastenable diaper pants without using adhesive to join the discrete fastener component to the second waist belt.

SUMMARY OF THE INVENTION

Aspects of the present disclosure include a method for assembling refastenable absorbent articles, each absorbent article comprises a chassis having a topsheet, backsheet, and an absorbent core disposed between the topsheet and the backsheet, wherein the chassis defines a first waist region longitudinally opposed to a second waist region, and having a longitudinal axis and a lateral axis, each absorbent article further comprises a first waist belt connected with the first waist region and a second waist belt connected with the second waist region, wherein a first discrete fastener component joins first end regions of the first and second waist belts and a second discrete fastener component joins second end regions of the first and second waist belts, wherein the first and second discrete fastener components are refastenably connected with the first waist belt and permanently connected with the second waist belt, the method comprising the steps of: advancing discrete chassis in a machine direction; advancing discrete fastener components in the machine direction, wherein each discrete fastener defines a first surface and a second surface, and a first end region and an opposing second end region separated by a central region, wherein a first fastener element is located in the first end region and a second fastener element is located in the second end region; advancing a first waist belt web in the machine direction, wherein the first waist belt web defines a first surface and a second surface; advancing a second waist belt web in the machine direction, wherein the second waist belt web defines a first surface and a second surface; orienting each discrete chassis such that the lateral axis is parallel with the machine direction; combining the first waist region of the chassis intermittently along the first surface of the first waist belt web and combining the second waist region of the chassis intermittently along the first surface of the second waist belt web; combining the first surface of the discrete fastener component with the first surface of the second waist belt web, wherein the discrete fastener component is positioned between adjacent chassis; folding the chassis to position the first waist region of the chassis into a face-to-face relationship with the second waist region of the chassis using a folding apparatus, wherein the second surface of the discrete fastener component is in a face-to-face relationship with the folding apparatus; bonding the second surface of the discrete fastener component to the first waist belt web; and cutting the first and second waist belt webs in a cross direction along the central region of the discrete fastener component to form a first absorbent article having a first discrete fastener component and a second absorbent article having a second discrete fastener component, wherein the first discrete fastener component comprises the first fastener element and the second discrete fastener component comprises the second fastener element.

Aspects of the present disclosure include a method for assembling refastenable absorbent articles, the method comprising the steps of: advancing a continuous length of chassis assemblies in a machine direction; cutting the continuous length of chassis assemblies into discrete chassis; advancing the discrete chassis in the machine direction onto a carrier apparatus, wherein the carrier apparatus comprises a frame rotatable about an axis of rotation, and a transfer member connected with the frame, wherein the transfer member is rotatable about a second axis of rotation that is orthogonal to the first axis of rotation, wherein the transfer member has a first portion and a second portion, wherein the topsheet of the discrete chassis contacts the first portion of the transfer member; advancing a continuous length of fastener assemblies in the machine direction; cutting the continuous length of fastener assemblies into discrete fastener components, wherein each discrete fastener component define a first surface and a second surface, each discrete fastener component comprising a first end region and an opposing second end region separated by a central region; advancing the discrete fastener components in the machine direction onto the carrier apparatus, wherein the second surface of the discrete fastener component contacts the second member of the transfer member, wherein the discrete fastener component is positioned adjacent to the chassis; advancing a first waist belt web in the machine direction, wherein the first waist belt web defines a first surface and a second surface; advancing a second waist belt web in the machine direction, wherein the second waist belt web defines a first surface and a second surface; reorienting the discrete chassis such that the lateral axis is parallel with the machine direction by rotating the transfer member about the second axis of rotation; combining the first waist region of the chassis intermittently along the first surface of the first waist belt web, the second waist region of the chassis intermittently along the first surface of the second waist belt; combining the first surface of the discrete fastener component to the first surface of the second waist belt web; folding the chassis to position the first waist region of the chassis into a face-to-face relationship with the second waist region of the chassis using a folding apparatus, wherein the second surface of the discrete fastener component is in a face-to-face relationship with the folding apparatus; bonding the second surface of the discrete fastener component with the first waist belt web; and cutting the first and second waist belt webs in a cross direction along the central region of the discrete fastener component to form a first absorbent article having a first discrete fastener component and a second absorbent article having a second discrete fastener component.

An apparatus for forming a refastenable absorbent article, the apparatus comprises a frame rotatable about an axis of rotation and a transfer member connected with the frame and extending radially outward from the frame. The transfer member is rotatable about a second axis of rotation that is orthogonal to the first axis of rotation. The transfer member comprises a first portion and a second portion, wherein the portion defines a first end region and a second end region separated by a central region, wherein the second portion comprises a proximal region and a distal region, wherein the proximal region of the second portion is connected with the first end region of the first portion such that the second portion forms an arm extending from the first portion of the transfer member. The transfer member defines an outer surface located at the farthest radially outward surface of the transfer member, wherein the first and second portions each have an outer surface that forms the outer surface of the transfer member.

BRIEF DESCRIPTION OF THE DRAWINGS

FIG. 11A is a schematic, plan view of a transfer member of a carrier apparatus taken along line C-C of FIG. 8.
FIG. 11B is a schematic, plan view of a transfer member of a carrier apparatus taken along line E-E of FIG. 8.

DETAILED DESCRIPTION OF THE INVENTION

Figure 1:
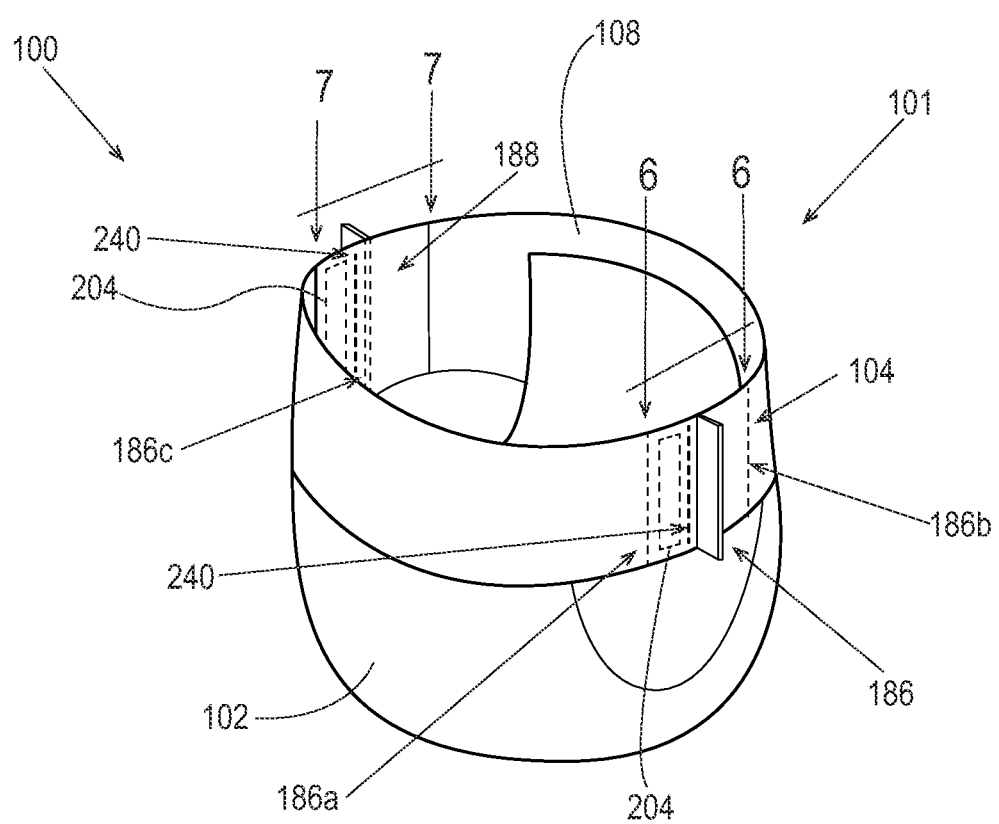
FIG. 1 is a schematic, perspective side view of a pre-fastened, refastenable pant.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (for example, they are intended to be discarded after a single use and may also be configured to be recycled, composted or otherwise disposed of in an environmentally compatible manner).

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Pant" (also referred to commercially as "training pant", "pre-closed diaper", "pant diaper", "diaper pant", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (for example, seams, heat bonds, pressure welds, adhesives, cohesive bonds, mechanical fasteners, etc.). A pant can be preformed anywhere along the circumference of the article in the waist region (for example, side fastened or seamed, front waist fastened or seamed, rear waist fastened or seamed).

"Pre-fastened" refers herein to pants manufactured and provided to consumers in a configuration wherein the front waist region and the back waist region are fastened or connected to each other as packaged, prior to being applied to the wearer. As such pants may have a continuous perimeter waist opening and continuous perimeter leg openings designed for infant or adult wearers. As discussed in more detail below, a pant can be preformed by various techniques including, but not limited to, joining together portions of the diaper using refastenable and/or permanent closure members (for example, seams, heat bonds, pressure welds, adhesives, cohesive bonds, mechanical fasteners, etc.). In addition, pants can be preformed anywhere along the circumference of the waist region (for example, side fastened or connected, front waist fastened or connected, rear waist fastened or connected).

The present disclosure relates to methods and apparatuses for manufacturing absorbent articles, and in particular, methods for assembling pre-fastened refastenable pants. As discussed in more detail below, pre-fastened pants may include a chassis having a first waist region and a longitudinally opposed second waist region. The chassis may also include a longitudinal axis and a lateral axis, wherein the longitudinal axis extends through the first and second waist regions. Each pant may further include a first waist belt connected with the first waist region of the chassis and a second waist belt connected with the second waist region of the chassis. A first discrete fastener component may be connected with a first end region of the first and second waist belts and a second discrete fastener component may be connected with a second end region of the first and second waist belts. The first and second discrete fastener components may each be permanently connected with the second waist belt and refastenably connected with the first waist belt.

A method of assembling pre-fastened, refastenable pants may include advancing discrete chassis in a machine direction and advancing discrete fastener components in the machine direction. The method may include advancing first and second waist belt webs in the machine direction. The chassis may be oriented such that the lateral axis is parallel with the machine direction. The first waist region of the chassis may be intermittently joined with the first waist belt web and the second waist region of the chassis may be joined with the second waist belt web. The discrete fastener component may be joined with the first surface of the first waist belt web using adhesive. The discrete fastener component is positioned between adjacent chassis. Next, the chassis may be folded to position the first waist region of the chassis into a face-to-face relationship with the second waist region of the chassis. Then, the discrete fastener component may be bonded to the second waist belt web. Lastly, the first and second waist belt webs may be cut in a cross direction along the central region of the discrete fastener component to form a first diaper having a first discrete fastener component and a second diaper having a second fastener discrete fastener component. The first discrete fastener component comprises the first fastener element and the second discrete fastener component comprises the second fastener element. The first and second fastener elements may comprise hook and loop fasteners, buttons, snaps, tab and slot fasteners, tape fasteners, adhesive fasteners, cohesive fasteners, magnetic fasteners, hermaphrodidic fasteners, and combinations thereof.

A converting apparatus for assembling pre-fastened, refastenable pants may include a carrier apparatus. The carrier apparatus may comprise a frame rotatable about an axis of rotation and a transfer member connected with the frame and extending radially outward from the frame. The transfer member is rotatable about a second axis of rotation that is orthogonal to the first axis of rotation. The transfer member comprises a first portion and a second portion, wherein the portion defines a first end region and a second end region separated by a central region, wherein the second portion comprises a proximal region and a distal region. The proximal region of the second portion is connected with the first end region of the first portion such that the second portion forms an arm extending from the first portion of the transfer member. The transfer member defines an outer surface located at the farthest radially outward surface of the transfer member, wherein the first and second portions each have an outer surface that forms the outer surface of the transfer member.

As previously mentioned, the processes and apparatuses disclosed herein may be used to assemble refastenable absorbent articles, and more particularly, pre-fastened refastenable pants. While it is to be appreciated that the methods and apparatuses disclosed herein may be used to assemble pre-fastened, refastenable pants, it is to be appreciated that the methods and apparatuses disclosed herein may be used to manufacture various types of absorbent articles. To help provide additional context to the subsequent discussion, the following provides a general description of absorbent articles in the form of pants that may be assembled in accordance with the methods and apparatuses disclosed herein.

Figure 2:
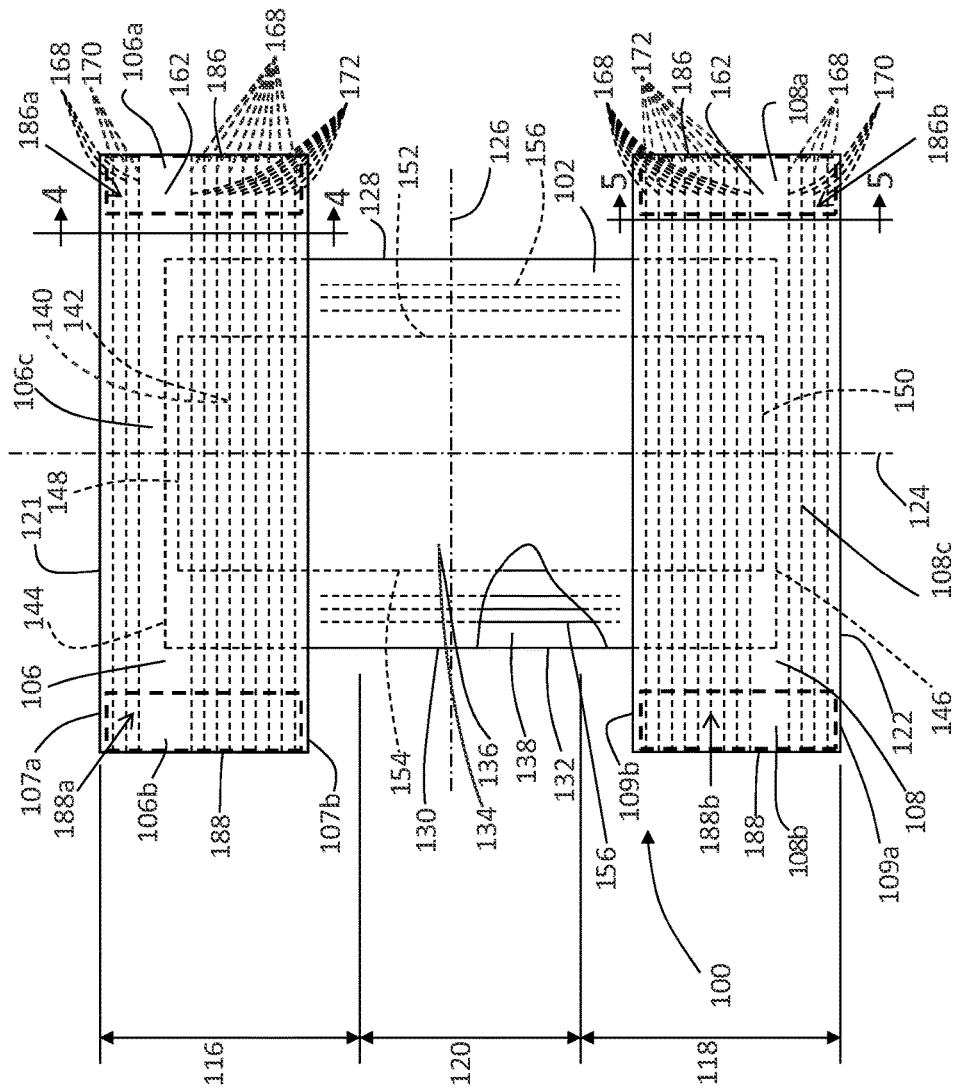
FIG. 2 is a schematic, plan view of a refastenable pant.

FIGS. 1 and 2 show examples of an absorbent article 100 in the form of a pant 101 that may be assembled in accordance with the apparatuses and methods disclosed herein. FIG. 2 shows a plan view of the pant 101 with the portion of the diaper that faces away from a wearer oriented toward the viewer. The pant 101 shown in FIGS. 1 and 2 includes a chassis 102 and a ring-like waist belt 104.

With continued reference to FIG. 2, the chassis 102 includes a first waist region 116 longitudinally opposing a second waist region 118 and a crotch region 120 disposed intermediate the first and second waist regions 116 and 118. The first waist region 116 may be configured as a front waist region and the second waist region 118 may be configured as back waist region. In some exemplary configurations, the length of each of the front waist region 116, back waist region 118, and crotch region 120 may be one-third of the length of the pant 101. The pant 101 may also include a laterally extending front waist edge 121 in the front waist region 116 and a longitudinally opposing and laterally extending back waist edge 122 in the back waist region 118. To provide a frame of reference for the present discussion, the pant 101 of FIG. 2 is shown with a longitudinal axis 124 and a lateral axis 126.

As shown in FIGS. 1 and 2, the pant 101 may include an inner, wearer facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. The pant 101 may also include other features, such as elasticized leg elastics 156 and/or leg cuffs to enhance the fit around the legs of the wearer.

Figure 3:
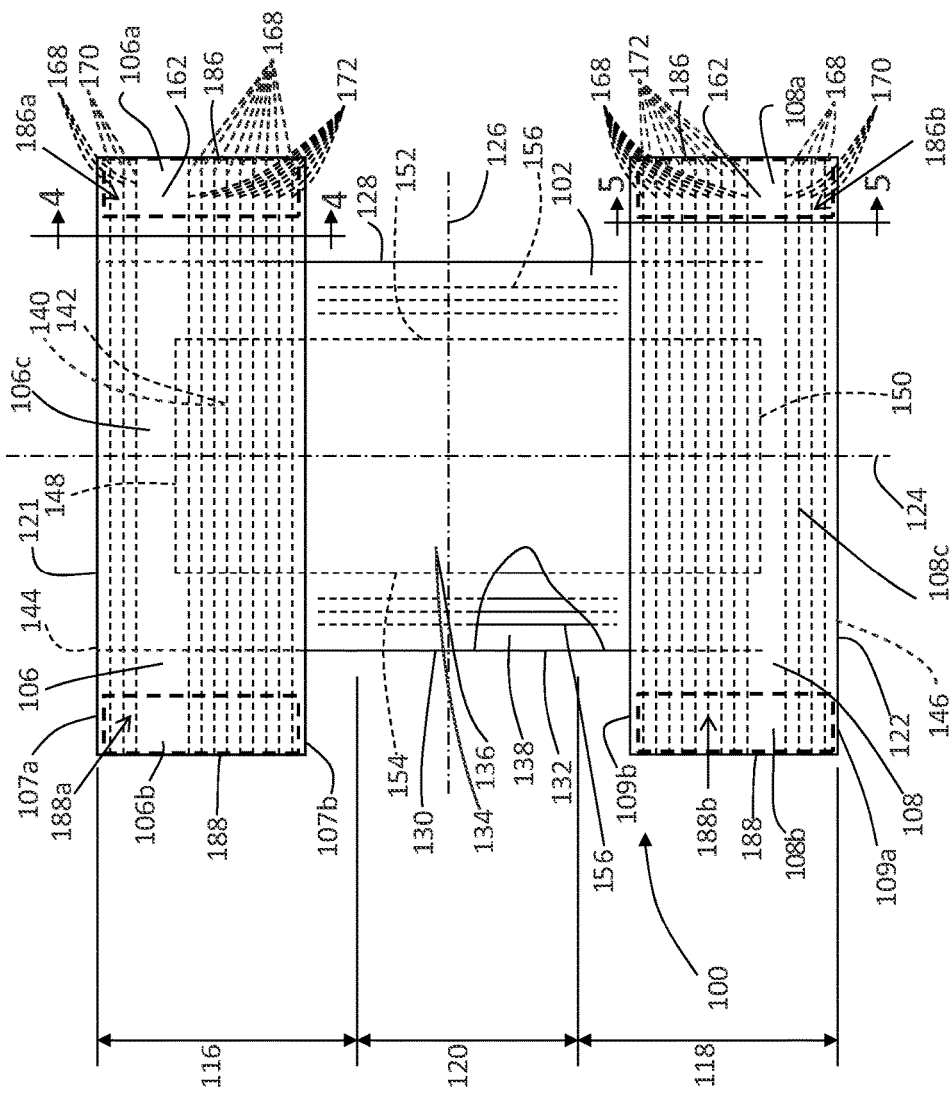
FIG. 3 is a schematic, plan view of a refastenable pant.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. In some exemplary configurations, as shown in FIG. 3, the laterally extending end edges 144 and 146 may also define the front and rear waist edges 121 and 122, respectively. With reference to FIG. 1, when the pant 101 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118. Referring to FIG. 1, pants 101 may be manufactured with a ring-like waist belt 104 and provided to consumers in a configuration wherein the front waist region 116 and the back waist region 118 are connected to each other as packaged, prior to being applied to the wearer. As such, pants 101 may have a continuous perimeter waist opening 110 and continuous perimeter leg openings 112. The ring-like waist belt 104 is defined by a first waist belt 106 connected with a second waist belt 108. As shown in FIG. 2, the first waist belt 106 defines first and second laterally opposing end regions 106a, 106b and a central region 106c, and the second elastic 108 belt defines first and second laterally opposing end regions 108a, 108b and a central region 108c. As shown in FIG. 2, the central region 106c of the first waist belt 106 is connected with the first waist region 116 of the chassis 102, and the central region 108c of the second waist belt 108 is connected with the second waist region 118 of the chassis 102.

Figure 4:
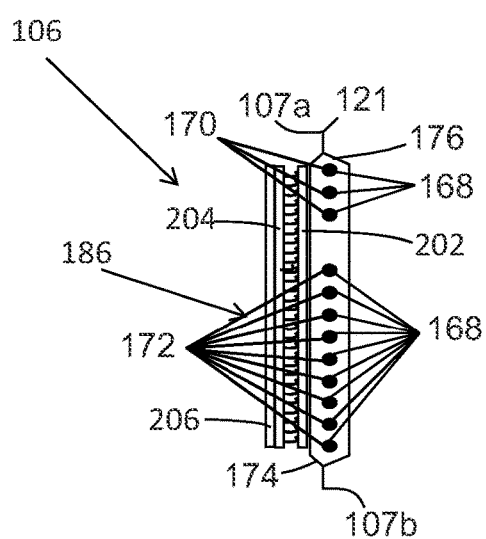
FIG. 4 is a schematic, sectional view of a portion of the refastenable pant of FIGS. 2 and 3 taken along line 4-4.
Figure 5:
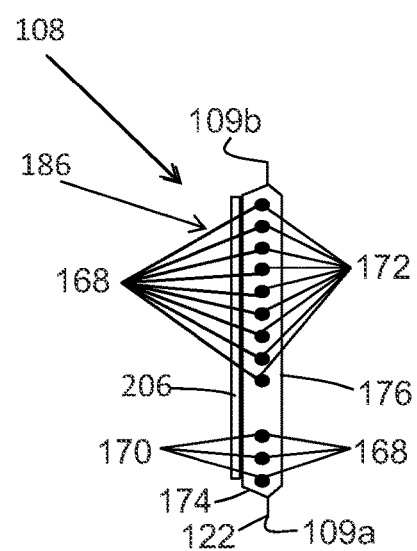
FIG. 5 is a schematic, sectional view of a portion of the refastenable pant of FIGS. 2 and 3 taken along line 5-5.

Referring to FIGS. 2, 4, and 5, the first waist belt 106 also defines an outer lateral edge 107a and an inner lateral edge 107b, and the second waist belt 108 defines an outer lateral edge 109a and an inner lateral edge 109b. The outer lateral edges 107a, 109a may also define the front waist edge 121 and the laterally extending back waist edge 122. The first waist belt 106 and the second waist belt 108 may also each include an outer, garment facing layer 176 and an inner, wearer facing layer 174.

It should also be appreciated that the first waist belt 106 and the second waist belt 108 may be constructed from various materials. For example, the first and second belts may include materials such as plastic films; apertured plastic films; woven or nonwoven webs of natural materials (for example, wood or cotton fibers), synthetic fibers (for example, polyolefins, polyamides, polyester, polyethylene, or polypropylene fibers) or a combination of natural and/or synthetic fibers; or coated woven or nonwoven webs. In some embodiments, the first and second waist belts include a nonwoven web of synthetic fibers, and may include a stretchable nonwoven. In other embodiments, the first and second waist belts include an inner hydrophobic, non-stretchable nonwoven material and an outer hydrophobic, non-stretchable nonwoven material. The first waist belt 106 and the second waist belt 108 may comprise the same materials and/or may have the same structure. In other embodiments, the first waist belt 106 and the second waist belt 108 may comprise different materials and/or may have different structures.

The first and second waist belts 106 and 108 may also each include elastic material such as elastic strands, ribbons, or films, interposed between the outer layer 176 and the inner layer 174. As shown in FIGS. 2, 4, and 5, the belt elastic material may include a plurality of elastic strands 168 which may be referred to herein as outer, waist elastics 170 and inner, waist elastics 172. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like waist belt 104.

As shown in FIGS. 1 and 2, a first discrete fastener component 186 joins the first waist belt 106 with the second waist belt 108, and a second discrete fastener component 188 joins the first waist belt 106 with the second waist belt 108 to define the ring-like waist belt 104 as well as the waist opening 110 and leg openings 112. The first discrete fastener component 186 includes a first end region 186*a*, a second end region 186*b*, and a central region 186*c* laterally separating the first and second end regions 186*a* and 186*b*. The second discrete fastener component 188 includes a first end region 188*a*, a second end region 188*b*, and a central region 188*c* laterally separating the first and second end regions 188*a* and 188*b*. In particular, the first region 186*a* of the first discrete fastener component 186 is connected with the first end region 106*a* of the first waist belt and the second region 186*b* of the first discrete fastener component 186 is connected with the first end region 108*a* of the second waist belt 108. Likewise, the first region 188*a* of the second discrete fastener component 188 is connected with the second end region 106*b* of the first waist belt 106 and the second region 188*b* of the second discrete fastener component 188 is connected with the second end region 108*b* of the second waist belt 108.

In some exemplary configurations, the first and second discrete fastener components 186 and 188 may each be permanently connected with the second waist belt 108 and may be refastenably connected with the first waist belt 106. The ability to refasten an initially pre-fastened pant may offer convenience to the caregiver. In some instances, it may be more convenient to apply the absorbent article like a traditional tape style diaper when away from home or when it is inconvenient to remove the clothing and/or shoes. Because it is difficult to predict when a change will be necessary and therefore when a particular mode of application will be needed, it is beneficial to have a disposable pant that is adaptable to being applied either as a traditional tape style diaper or as a disposable pant, pull-on. In addition, an absorbent article that can be applied like a traditional tape style diaper or a disposable pant also permits inspection of the interior of the product without having to pull the product down. These refastenable structures may also provide dual functionality enabling the wrapping and disposal of the used product.

As shown in FIGS. 1 and 4-7, the first and second discrete fastener components 186 and 188 each include a connection element 202, a fastener element 204, and a side panel 206. Each side panel 206 may define a first end region 208, a second end region 210, and a central region 212 separating the first and second end regions 208 and 210. The side panel 206 may define a first surface 214 and a second surface 216. The fastener element 204 may define a first surface 218 and an opposing second surface 220. The connection element 202 may also define a first surface 222 and a second surface 224.

Figure 6:
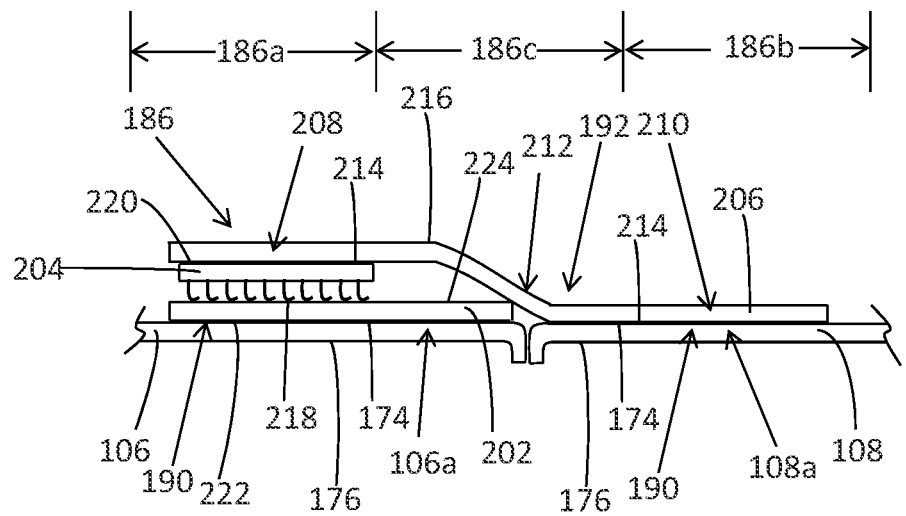
FIG. 6 is a schematic, plan view of a portion of the pre-fastened refastenable pant of FIG. 1 taken along line 6-6.
Figure 7:
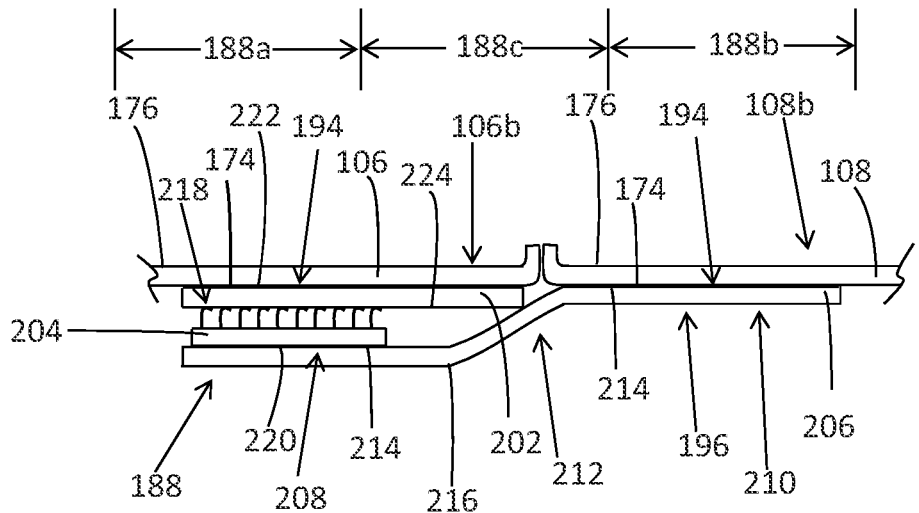
FIG. 7 is a schematic, plan view of a portion of the pre-fastened refastenable pant of FIG. 1 taken along line 7-7.

As shown in FIGS. 6 and 7, the first surface 214 of the side panels 206 may be connected with the second surface 220 of the fastener elements 204. The first surface 218 of the fastener elements 204 may be connected with the second surface 224 of the connection elements 202. In some exemplary configurations, the first surfaces 190 and 194 of the first and second discrete fastener components 186 and 188, respectively, may be connected with the first and second waist belts 106 and 108, and the second surfaces 192 and 196 of the first and second discrete fastener components 186 and 188 may face the wearer. In particular, the first surface 222 of the connection elements 202 may be connected with the inner, wearer facing layer 174 of the end regions 106*a* and 106*b* of the first waist belt 106. The first surface 214 of the side panels 206 may be connected with the inner, wearing facing layer 174 of the end regions 108*a* and 108*b* of the second waist belt 108.

In some exemplary configurations, such as shown in FIGS. 1-7, the first and second fastener elements 186 and 188 may be configured to refastenably connect with the first waist belt 106. Particularly, the fastener elements 204 may be refastenably connected with the connection elements 202 that are connected with the first waist belt 106 such that the fastener element 204 may engage and disengage from the connection element 202 over multiple cycles. It is to be appreciated that the first and second fastener elements 186 and 188 may be configured to refastenably connect with the second waist belt 108 and/or the first waist belt 106. It is to be appreciated that the first and second discrete fastener components 186 and 188 may be connected with the first and second waist belts 106 and 108 in various ways. It is to be appreciated that the first and second discrete fastener components 186 and 188 may be connected with the first waist belt 106 in various configurations, such as adhesives, cohesives, thermal bonding, ultrasonic bonding, mechanical bonding, and mechanical fastening e.g. hook and loop type fasteners, tape tab fasteners, and the like. For example, the first and second discrete fastener components 186 and 188 may be permanently bonded, releasably connected, and/or refastenably connected with the inner, wearer facing layer 174 of the second waist belt 108, with for example, cohesives, thermal bonding, ultrasonic bonding, mechanical bonding, and mechanical fastening e.g. hook and loop type fasteners, tape tab fasteners, and the like. Exemplary bond types may include discrete bonds such as sonic sealed bonds, heat sealed bonds, high pressure bonds, radio frequency bonds, adhesive or cohesive bonds, sewn bonds, autogeneous bonds, and combinations thereof. The first and second fastener components 186 and 188 may be joined with the second waist belt 108 in a predetermined pattern of heat/pressure or ultrasonic welds which withstand the forces and stresses exacted onto seam during application and wear of the pant. Methods and apparatuses for forming seams using hot air are described in U.S. patent application Ser. No. 13/402,056, filed Feb. 22, 2012.

The side panels 206 may be substantially rectangular in shape or the side panels may be shaped in such a way as to provide an integral tab for ease of opening and refastening. The side panels 206 may also be extensible in at least the lateral direction. The side panels 206 may also be elastically extensible in the lateral direction. Furthermore, the side panels 206 may be elastically extensible in both the longitudinal and lateral directions. The side panels 206 may comprise a film, a nonwoven or a combination of film and nonwoven. The side panels 206 may also comprise a plurality of strand-like filaments and a nonwoven. The strand-like elements may also be elastically extensible in at least the lateral direction.

It is to be appreciated that the side panels 206 may include various types of materials. The side panels may include plastic films; apertured plastic films; nonwoven or nonwoven webs of natural materials (e.g., wood or cotton fibers); synthetic fibers (e.g., polyolefins, polyamides, polyester, polyethylene, and/or polypropylene fibers); or combinations of natural and/or synthetic fibers; or coated woven or nonwoven webs. In some embodiment, the side panels may include a stretchable nonwoven. In other embodiments, the side panels may include an inner hydrophobic non-stretchable nonwoven material and an outer hydrophobic, non-stretchable nonwoven material. In addition, the side panels may include elastic elements such as strand or films.

The fastener elements 204 may comprise various types of refastenably engageable fastening structures. For example, the fastener elements 204 may include mechanical fasteners, in the form of hook and loop fasteners, hook and hook fasteners, macrofasteners, buttons, snaps, tab and slot fasteners, tape fasteners, adhesive fasteners, cohesive fasteners, magnetic fasteners, hermaphrodidic fasteners, and the like. Some examples of fastening systems and/or fastening components 186, 188 are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 and 2007/0093769.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (for example, Wiley® mill), and a representative sample of suitable mass taken from the randomly mixed particles.

Figure 8:
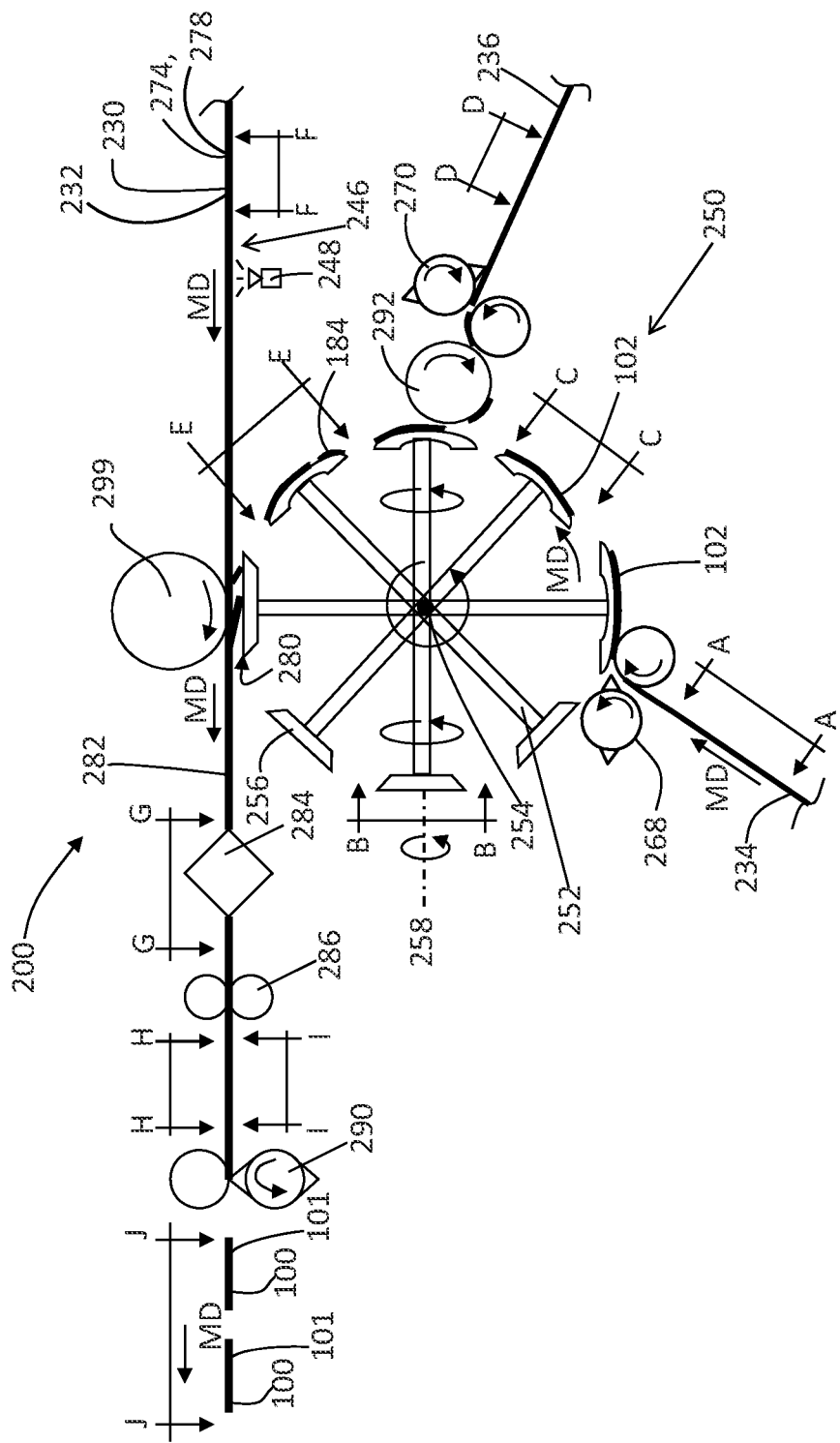
FIG. 8 is a schematic, side elevation view of a converting apparatus adopted to assemble pre-fastened refastenable absorbent articles.

As previously mentioned, the apparatuses and methods according to the present disclosure may be utilized to assemble various components of pre-fastened, refastenable pants. For example, FIG. 8 shows a schematic view of a converting apparatus 200 adapted to manufacture pants. The method of operation of the converting apparatus may be described with reference to the various components of pants described above and shown in FIGS. 1-7. Although the following methods are provided in the context of the pant shown in FIGS. 1 and 2, it is to be appreciated that various embodiments of pants can be manufactured according to the methods disclosed herein, such as for example, the absorbent articles disclosed in U.S. Pat. No. 7,569,039; U.S. Patent Publication Nos. 2005/0107764A1, 2012/0061016, and 2012/0061015.

As described in more detail below, with reference to FIGS. 1, 2, and 8, the converting apparatus 200 operates to advance discrete chassis 102 along a machine direction MD such that the lateral axis 126 of each chassis 102 is parallel with the machine direction MD, and wherein the chassis 102 are spaced apart from each other along the machine direction MD. Opposing first and second waist regions 116 and 118 of the spaced apart chassis 102 are then connected with continuous lengths of advancing first and second waist belt web 230 and 232. The converting apparatus 200 also operates to advance fastener components 184 in the machine direction MD. The fastener components 184 are combined with the continuous length of first waist belt web 230 such that the fastener component 184 is positioned adjacent to the chassis 102. The chassis 102 are then folded along the lateral axis 126 to bring the first and second waist belt webs 230 and 232 into a facing relationship. The first and second waist belt webs 230 and 232 are joined together and the fastener components 184 are joined with the continuous length of second waist belt web 232. The fastener components 184 may be connected with the second belt substrate 231 at bond regions 288. The first and second waist belt webs 230 and 232 are cut along the fastener component 184 to create discrete diapers 101 having first and second discrete fastener components 186 and 188, such as shown in FIG. 1. As a result, the first and second discrete fastener components 186 and 188 are refastenably connected with the first waist belt 106.

Figure 9:
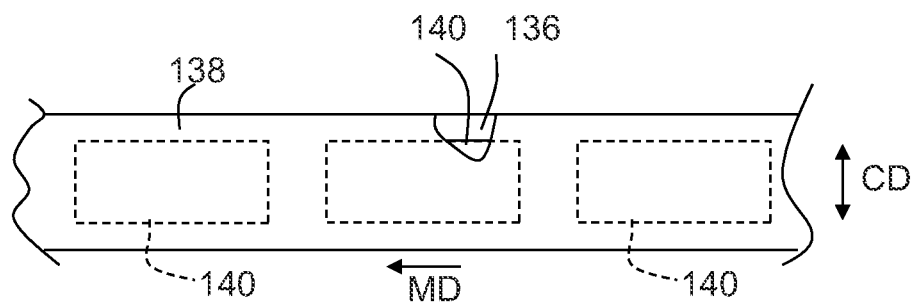
FIG. 9 is a schematic, plan view of a continuous length of chassis assemblies taken along line A-A of FIG. 8.

The converting apparatus 200 shown in FIG. 8 operates to advance a continuous length of chassis assemblies 234 in a machine direction MD to a carrier apparatus 250. As shown in FIG. 9, the continuous length of chassis assemblies 234 may include absorbent assemblies 140 sandwiched between the topsheet 138 and the backsheet 136, leg elastics, barrier leg cuffs and the like. The continuous length of chassis assemblies 234 may be cut into discrete chassis 102 by a cutting member 268 positioned adjacent to the carrier apparatus 250. In some exemplary configurations, the cutting member 268 may be configured to cut the continuous length of chassis assemblies 234 prior to the discrete chassis 102 advancing onto the carrier apparatus 250. In other exemplary configurations, the cutting member 268 may be configured to cut the continuous length of chassis assemblies 234 after the continuous length of chassis assemblies 234 advance onto the carrier apparatus 250.

Figure 10:
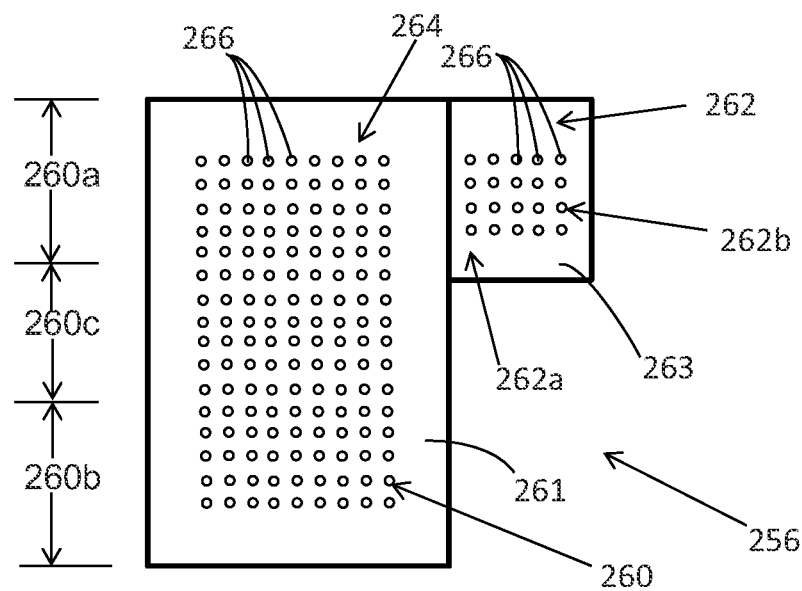
FIG. 10 is a schematic, plan view of a transfer member of a carrier apparatus taken along line B-B of FIG. 8.

As shown in FIG. 8, the carrier apparatus 250 may include a frame 252 that is rotatable about an axis of rotation 254 and a plurality of transfer members 256 rotatably connected with the frame 252. The transfer members 256 are configured to rotate about an axis of rotation 258 that is orthogonal to the axis of rotation 254 of the frame 252. The transfer member has an outer surface 264. In some exemplary configurations, such as shown in FIG. 10, each transfer member 256 may include a first portion 260 and a second portion 262, the first and second portions 260 and 262 each having an outer surface 261 and 263, respectively. The outer surfaces 261 and 263 form the outer surface 264 of the transfer member 256. The outer surfaces 261 and 263 may be substantially coplanar. The first portion 260 may define a first end region 260a, a second end region 260b, and a central region 260c separating the first and second end regions 260a and 260b. The second portion 262 may define a proximal end region 262a and a distal end region 262b. The proximal end region 262a of the second portion 262 may be connected with the first end region 260a of the first portion 260. The second portion 262 may be in the form of an arm that extends from the first end region 260a of the first portion 260. The outer surface 264 of the transfer members 256 may comprise vacuum apertures 266 that are in fluid communication with a vacuum source. The first and second portions 260 and 262 may have various shapes. For example, as shown in FIG. 10, the first and second portions may be rectangular. It is to be appreciated that the outer surface 264 of the transfer members 256 may be flat in one or more directions. Or, in other exemplary configurations, the outer surface 264 of the transfer member may be curved in one or more directions.

The discrete chassis 102 may advance in the machine direction MD onto the outer surface 264 of the transfer members 256. As shown in FIGS. 11A and 11B, the discrete chassis 102 may advance on the first portion 260 of the transfer member 256 with the inner, wearer facing surface 132 of the chassis 102 facing the outer surface 264 of the transfer member 256. As a result, the inner, wearing facing surface 132 of the chassis may remain free of potential contamination caused by materials, such as adhesive, falling onto the chassis 102 as the chassis 102 advances through the converting apparatus 200.

Figure 12:
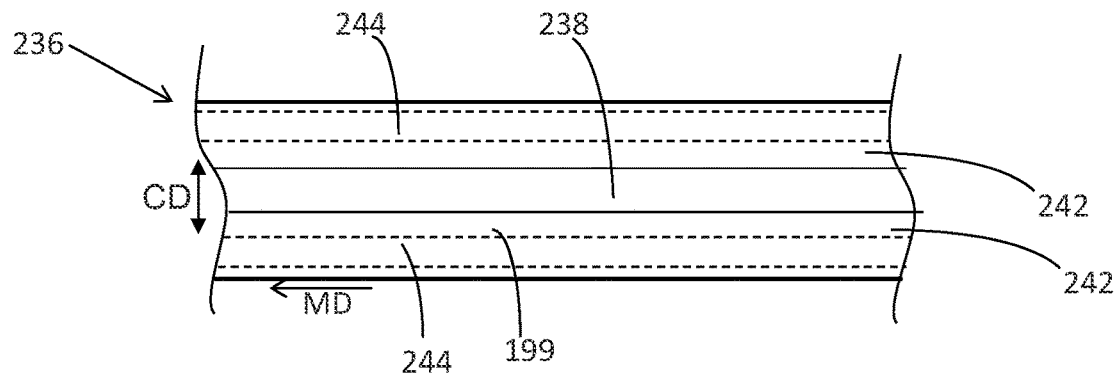
FIG. 12 is a schematic, plan view of a continuous length of fastener assemblies taken along line D-D of FIG. 8.
Figure 13:
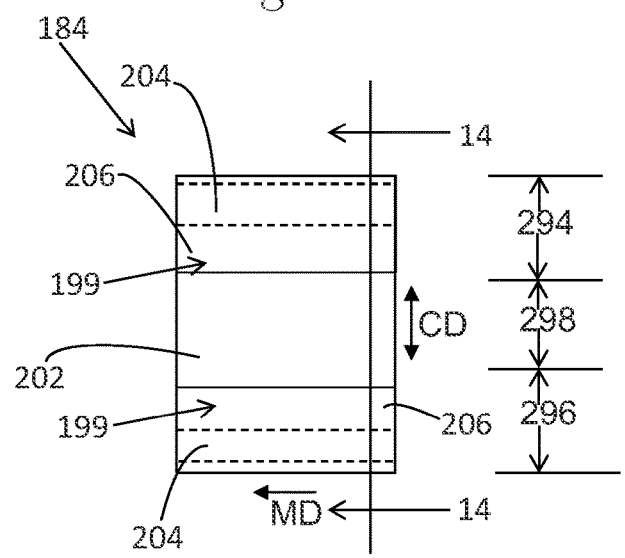
FIG. 13 is a schematic, plan view of a discrete fastener component.

In some exemplary configurations, as the chassis 102 advances in the machine direction MD on the carrier apparatus 250, a continuous length of fastener assemblies 236 advances in the machine direction MD to the carrier apparatus 250. In some exemplary configurations, such as shown in FIG. 12, the continuous length of fastener assemblies 236 may include a continuous length of connection elements 238, two continuous lengths of side panels 242, and two continuous lengths of fastener elements 244.

With reference to FIGS. 8, 12-14A, as the continuous length of fastener assemblies 236 advances in the machine direction MD, a cutting member 270 positioned adjacent to the carrier apparatus 250 operates to cut the continuous length of fastener assemblies 236 in the cross direction CD into discrete fastener components 184. The discrete fastener component 184 may define a first surface 198 and an opposing second surface 199. The discrete fastener component 184 may advance from the cutting member 270 to the transfer roll 292 shown in FIG. 8. The transfer roll 292 may operate to space adjacent discrete fastener components 184 from each other in the machine direction MD. As a result, the discrete fastener components 184 may be properly spaced apart in preparation for transferring the discrete fastener components 184 to the carrier apparatus 250. Exemplary methods and apparatuses for spacing components are described in U.S. Pat. Nos. 5,702,551 and 6,450,321; and U.S. Patent Publication No. 2012/0152447.

Figure 14A:
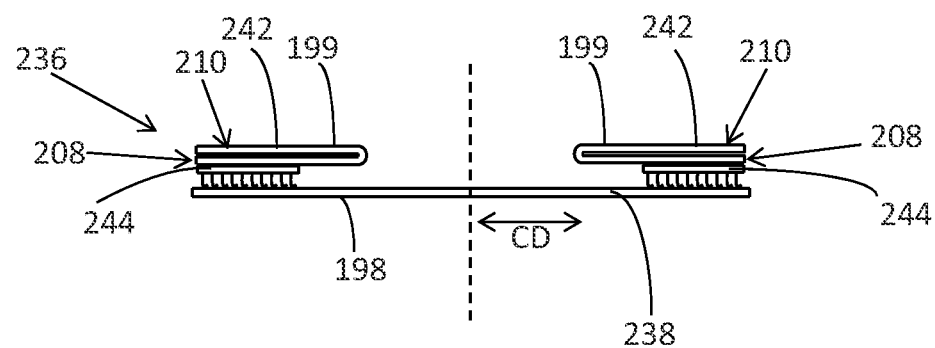
FIG. 14A is a schematic, sectional view of the discrete fastener component of FIG. 13 taken along line 14-14.
Figure 14B:
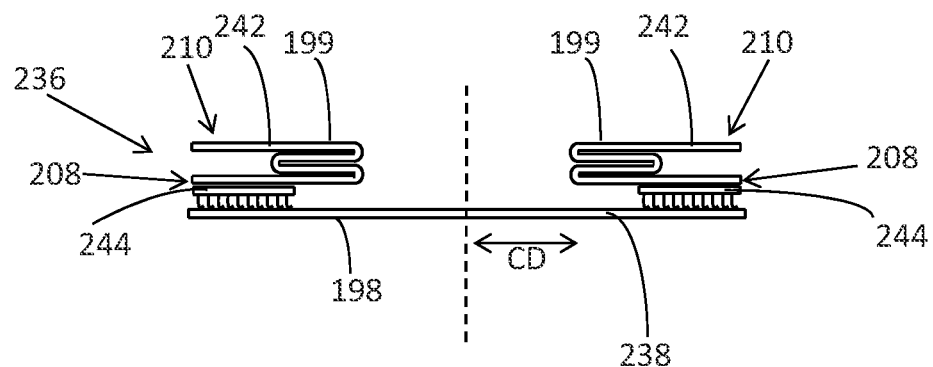
FIG. 14B is a schematic, sectional view of the discrete fastener component of FIG. 13 taken along line 14-14.

The discrete fastener component 184 may define a first end region 294, a second end region 296, and a central region 298 separating the first and second end regions 294 and 296 in the cross direction CD. The first end region 294 may comprise a first fastener element 204 and a first side panel 206 and the second end region 296 may comprise a second fastener element 204 and second side panel 206. As shown in FIG. 14A, in some exemplary configurations, the side panels 206 may be folded in a C-shape along a cross direction CD such that the first and second end regions 208 and 210 of the side panels 206 are in a face-to-face relationship. As shown in FIG. 14B, in other exemplary configurations, the side panels 206 may be folded into two or more C-folds. A connection element 202 extends from the first end region 294, through the central region 298, and to the second end region 296.

The discrete fastener components 184 are positioned on the second portion 262 of the transfer member 256 as shown in FIG. 11B. In some exemplary configurations, the second surface 199 of the discrete fastener component 184 may face the outer surface 264 of the transfer member 256. In some exemplary configurations, adhesive 246 may be applied to the second surface 199 of the discrete fastener components 184 using an adhesive applicator 248. In other exemplary configurations, the second surface 199 of the discrete fastener components 184 may be pre-glued prior to advancing onto the carrier apparatus 250.

Figure 15:
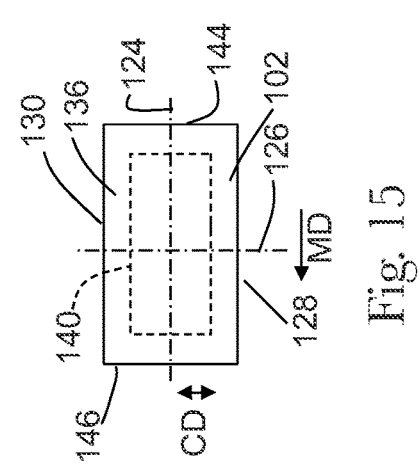
FIG. 15 is a schematic, plan view of a discrete chassis.

The carrier apparatus 250 advances the discrete chassis 102 in the machine direction MD from the orientation shown in FIG. 15, wherein the longitudinal axis 124 of the chassis 102 is generally parallel with the machine direction MD. The carrier apparatus also advances the discrete fastener component 184 in an orientation shown in FIG. 13, wherein the first end region 294 of the discrete fastener component 184 is separated from the second end region 296 of the discrete fastener component 184 in the cross direction CD. As the discrete chassis 102 advances in the machine direction MD, the carrier apparatus 250 may also rotate the discrete chassis 102 to an orientation shown in FIG. 16, wherein the lateral axis 126 is generally parallel with the machine direction MD. At the same time, the carrier apparatus 250 may rotate the discrete fastener component 184 to an orientation shown in FIG. 17, wherein the first end region 294 of the discrete fastener component 184 is separated from the second end region 296 of the discrete fastener component 184 in the machine direction MD. The carrier apparatus may also change the speed at which the chassis advances in the machine direction MD. It is to be appreciated that the carrier apparatus 250 may operate in various ways. The carrier apparatus may operate, for example, as described in U.S. patent application Ser. Nos. 13/447,531; 13/447,544; 13/447,568; and 13/447,585, all filed on Apr. 16, 2012.

While the chassis 102 shown in FIG. 15 is shown with the second laterally extending end edge 146 as a leading edge and the first laterally extending end edge 144 as the trailing edge, it is to be appreciated that in other embodiments, the chassis 102 advance in other orientations. For example, the chassis 102 may be oriented such that the second laterally extending end edge 146 is a trailing edge and the first laterally extending end edge 144 is a leading edge.

With reference to FIGS. 8, 16-19, the chassis 102 and discrete fastener components 184 are transferred from the carrier apparatus 250 and combined with advancing, continuous lengths of first and second waist belt webs 230 and 232. The first and second waist belt webs 230 and 232 each define a first surface, shown as inner, wearer facing surfaces 272 and 276, and a second surface, shown as outer, garment facing surfaces 274 and 278. The inner, wearer facing surface 272 of the first waist belt web 230 may be combined with the outer, garment facing surface 134 of the chassis 102 along the first waist region 116. Moreover, the inner, wearer facing surface 276 of the second waist belt web 232 may be combined with the outer, garment facing surface 134 of the chassis 102 along the second waist region 118. The inner, wearer facing surface 276 of the second waist belt web 232 may be combined with the second surface 199 of the discrete fastener component 184 such that discrete chassis 102 are positioned adjacent to discrete fastener components 184 and discrete fastener components 184 are separated by discrete chassis 102. As shown in FIG. 8, in some exemplary configurations, adhesive 246 may be applied to the inner, wearer facing surfaces 272 and 276 of the first and second waist belt webs 230 and 232 using an adhesive applicator 248 before combining with the discrete chassis 102 and discrete fastener components 184 at the nip 280 between nip roll 282 and the carrier apparatus 250.

Figure 19:
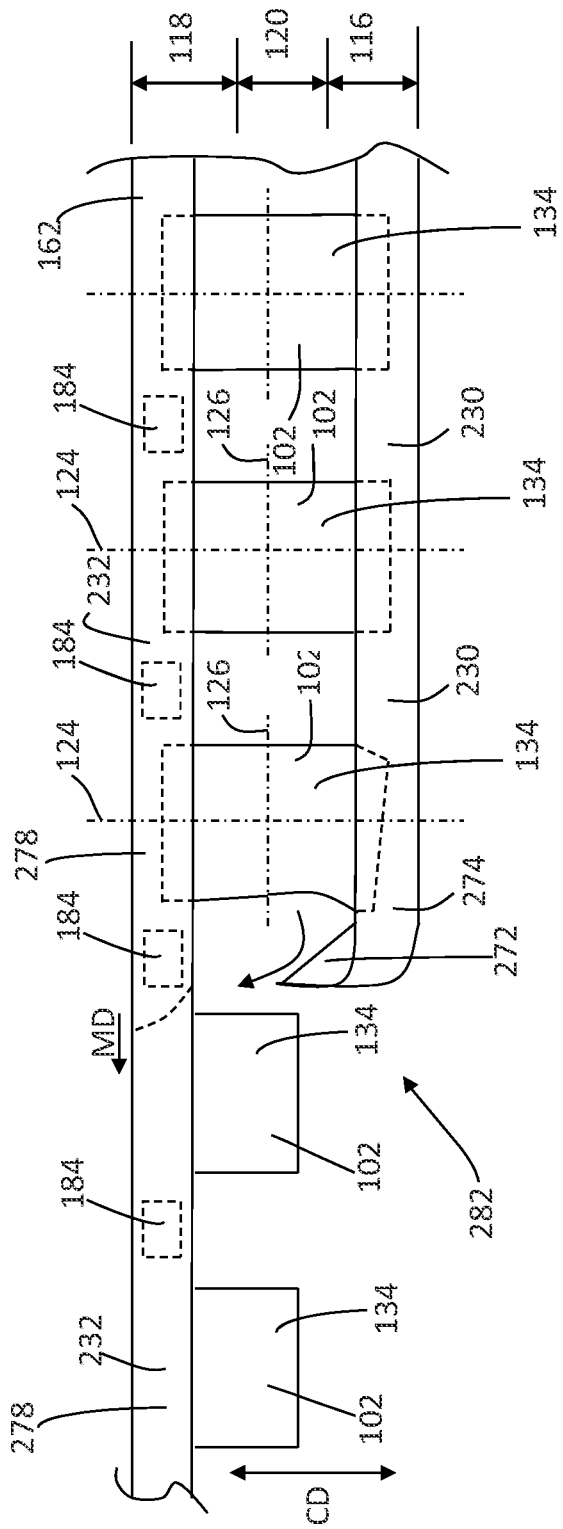
FIG. 19 is a continuous length of absorbent articles having discrete chassis intermittently spaced apart along continuous first and second continuous belt substrates and discrete fastener components joined with the first continuous belt substrate taken along line G-G of FIG. 8.
Figure 20:
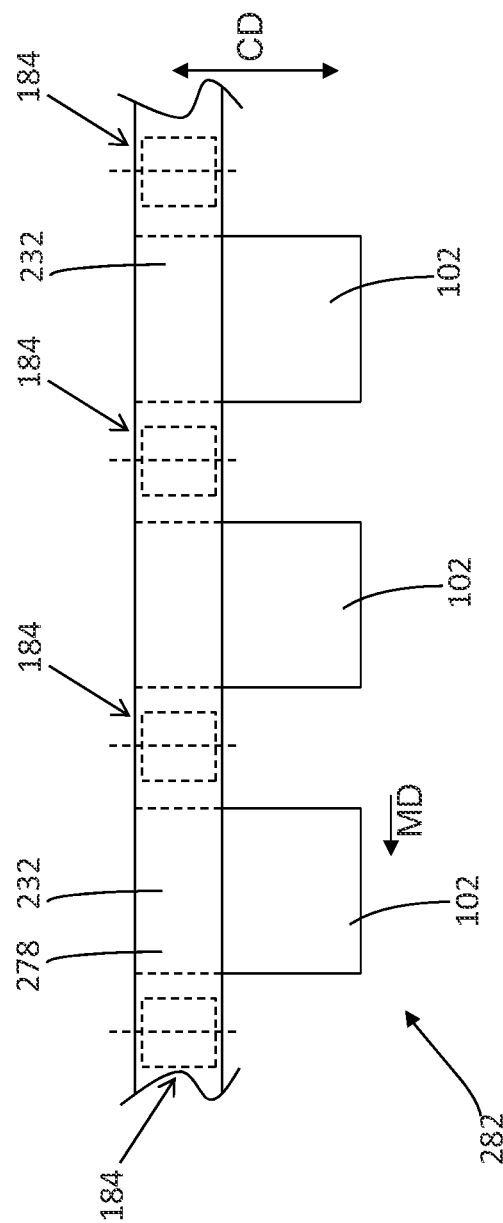
FIG. 20 is a continuous length of folded absorbent articles taken along line H-H of FIG. 8.

With reference to FIG. 19, a continuous length of absorbent articles 282 are defined by multiple discrete chassis 102 spaced from each other along the machine direction MD and connected with each other by the continuous lengths of first and second waist belt webs 230 and 232. Discrete fastener components 184 are positioned on the second waist belt web 232 between adjacent chassis 102. The discrete fastener components 184 may be spaced between adjacent chassis 102. In some exemplary configurations, the discrete fastener components 184 may be adjacent to the discrete chassis 102. Or, in other exemplary configurations, discrete fastener components 184 may be in contact with, and may overlap, the discrete chassis 102.

Figure 21:
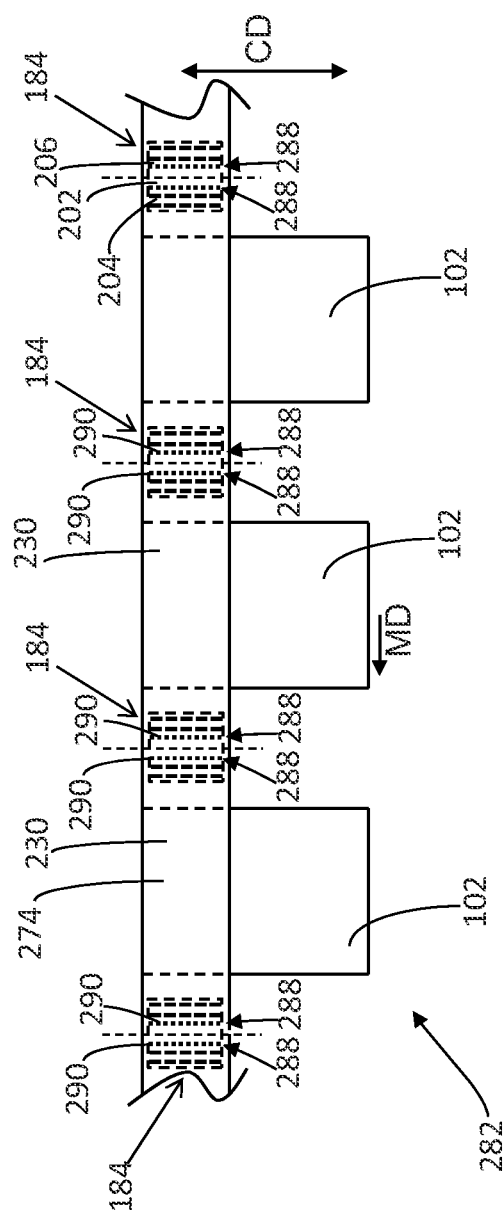
FIG. 21 is a continuous length of folded absorbent articles taken along line I-I of FIG. 8.
Figure 22:
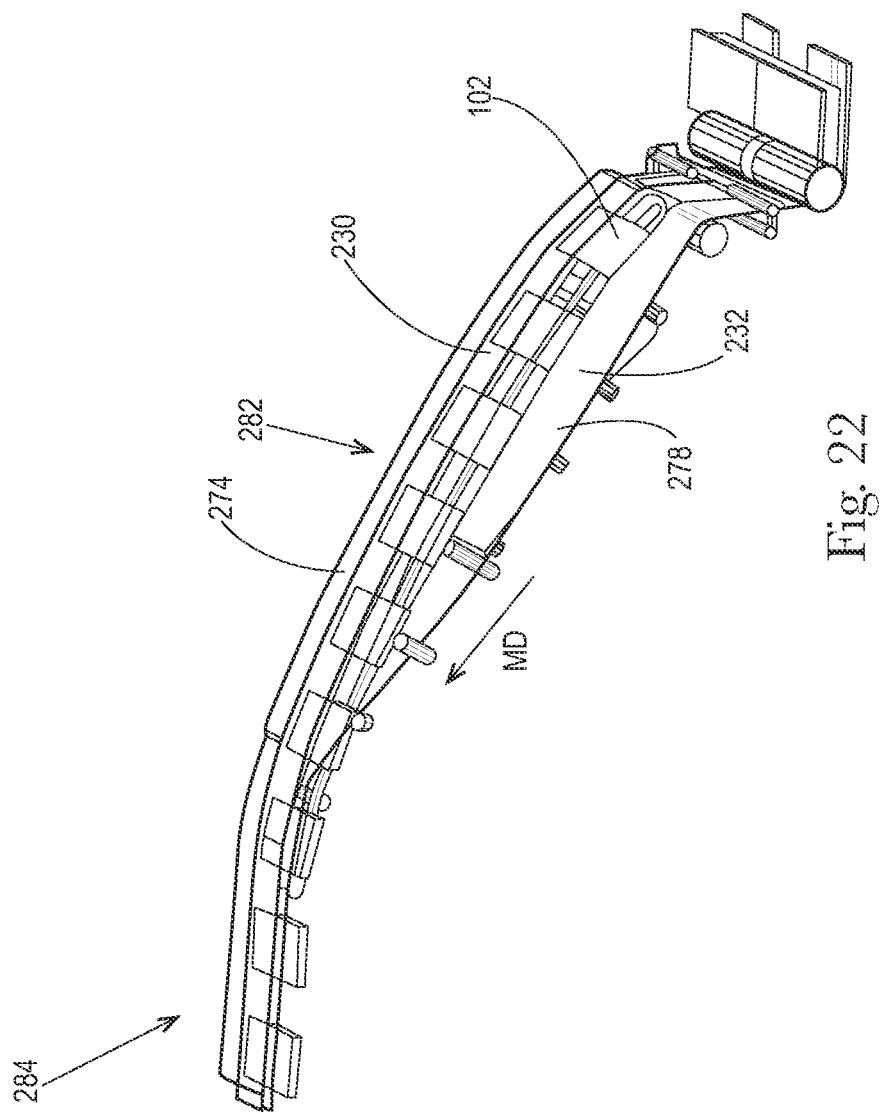
FIG. 22 is a perspective view of a folding apparatus.

As shown in FIG. 8, the continuous length of absorbent articles advances from the nip 280 to a folding apparatus 284. With reference to FIGS. 19-22, at the folding apparatus 284, each chassis 102 is folded in the cross direction CD along the lateral axis 126 to place the first waist region 116, and specifically, the inner, wearer facing surface 132 into a face-to-face relationship with the inner, wearer facing surface 132 of the second waist region 118. The folding of the chassis 102 also may position the inner, wearer facing surface 276 of the second waist belt web 232 extending between each chassis 102 in a facing relationship with the inner, wearer facing surface 272 of the first waist belt web 230 extending between each chassis 102. As a result, the discrete fastener components 184 connected with the second waist belt web 232 are brought into contact with the first waist belt web 232. Specifically, the first surface 298 of the discrete fastener component 184 is brought into contact with the inner, wearing facing surface 272 of the continuous length of first waist belt web 230. With reference to FIGS. 19 and 22, the discrete fastener component 184 may be positioned between the folding apparatus 284 and the inner, wearing facing surface 276 of the second waist belt web 232 during the folding process. As a result, the folding apparatus 284 may support the fastener component 184 and may prevent portions of the discrete fastener component 184 from unfolding or folding onto other portions of the discrete fastener component 184 during the folding process. However, as a result of supporting the first surface 198 of the discrete fastener component 184 with the folding apparatus 250, the first surface 198 of the discrete fastener component 184 may not comprise adhesive for joining the connection element 202 with the first waist belt web 230. Exemplary folding apparatuses are described in U.S. patent application Ser. No. 13/368,378, filed Feb. 8, 2012.

Figure 23:
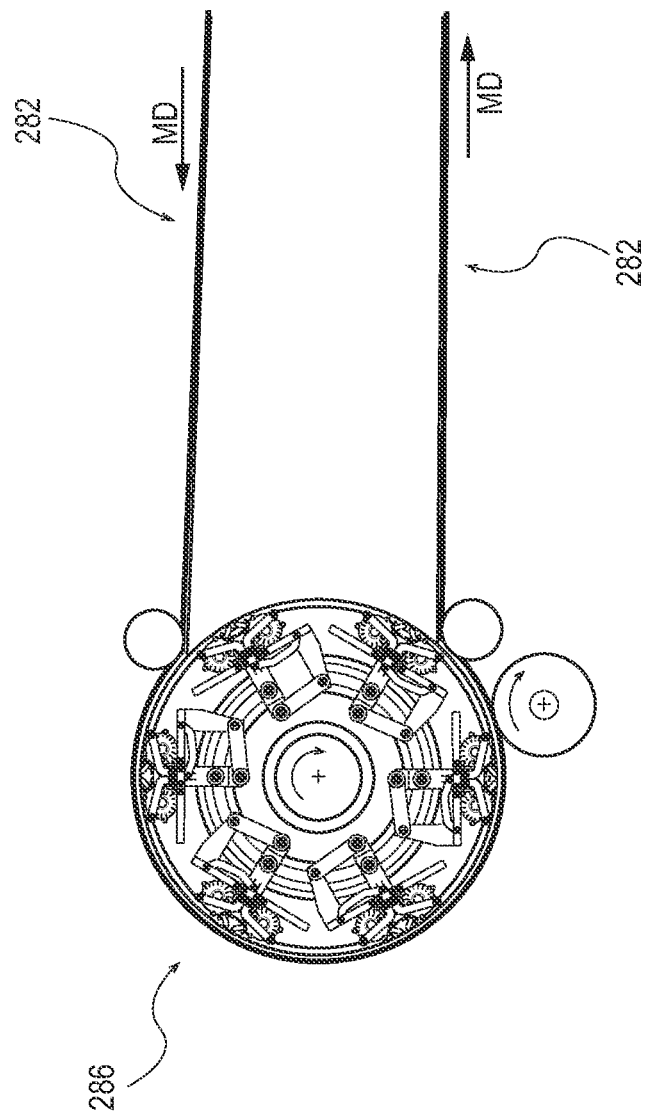
FIG. 23 is a schematic, side elevation view of a bonding apparatus.

As shown in FIGS. 8 and 23, the folded discrete chassis 102 connected with the first and second waist belt webs 230 and 232 are advanced from the folding apparatus 284 to a bonding apparatus 286. As shown in FIG. 21, the bonding apparatus 286 operates to bond a portion of the continuous length of first waist belt web 230 with a portion of the connection element 202, thus creating bond regions 288 of discrete bonds 290. In some exemplary configurations, two or more bond regions 288 of discrete bonds 290 may be formed between the first waist belt web 230 and the connection element 202. The discrete bonds 290 may permanently join the first waist belt web 230 with the connection elements 202 of the discrete fastener components 184. In some exemplary configurations, the bonding apparatus 286 may bond only the connection element 202 with the continuous length of first waist belt web 230. In other exemplary configurations, the bonding apparatus 286 may be configured to bond through multiple layers of the discrete fastener component 184. Exemplary methods of selectively bonding layers together are described, for example, in U.S. Patent Application No. 2012/0021186. While it is shown in FIG. 21 that the bond region 288 is located adjacent to the fastener element 204, it is to be appreciated that in some exemplary configurations, the connection element 202 may be bonded to the continuous length of first waist belt web 230 at a position on the connection element 202 where the fastener element 204 overlaps with the connection element 202.

It is to be appreciated that bonding the first waist belt web 230 with the connection element 202 using a method such as hot air bonding, eliminates the need to apply adhesive to the first surface 198 of the discrete fastener element 184 prior to folding the chassis 102. Moreover, with reference to FIG. 21, the continuous length of second waist belt web 232 may face the bonding apparatus 286 such that the bonding apparatus 286 supports the discrete fastener component 184 and the first waist belt web 230 until the discrete fastener component 184 and first waist belt web 230 are bonded together. Exemplary bonding apparatuses are described in U.S. patent application Ser. Nos. 13/402,056, filed Feb. 22, 2012; and 13/401,907, filed Feb. 22, 2012.

Figure 24:
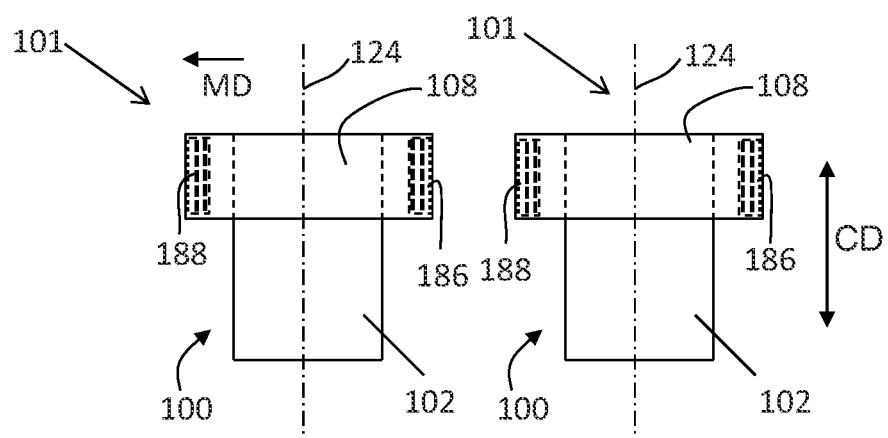
FIG. 24 is a schematic, plan view of discrete pre-fastened refastenable pants taken along line J-J of FIG. 8.

With reference to FIGS. 8 and 24, a continuous length of absorbent articles 282 are advanced from the bonding apparatus 286 to a cutting member 290 where the bond regions 288 are cut in the cross direction CD along the central region 298 of the discrete fastener component 184 to create a first discrete fastener component 186 on a discrete pant 101 and a second discrete fastener component 188 on a subsequently advancing discrete pant. It is to be appreciated that the cutting member 290 is configured to cut in the cross direction CD along the central region 298 of the discrete fastener component 184 without cutting the side panels 206 of the discrete fastener component 184. The cutting member 290 shown in FIG. 8 is in the form of a knife roll. It is to be appreciated that the cutting member 290 may be configured in various ways.

Figure 25:
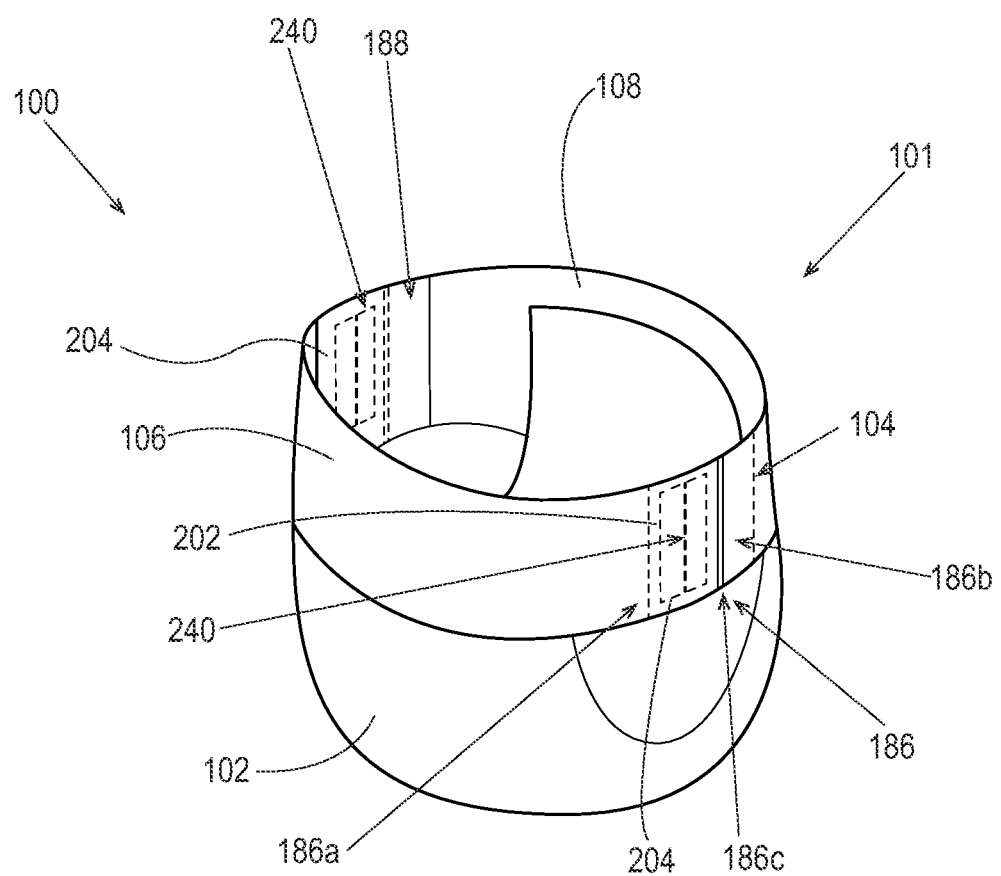
FIG. 25 is a schematic, perspective side view of a pre-fastened, refastenable pant.

As shown in FIG. 25, in an exemplary configurations such as shown in FIG. 14B where the side panels 206 are folded into two or more C-folds, the first and second waist belts 106 and 108 may be separated from each other. It is to be appreciated that the additional material of the side panels 206 that is folded into more than one C-fold allows for the separation between the first and second waist belts 106 and 108. In an exemplary configuration such as shown in FIG. 14A where the side panels 206 are folded into a single C-fold, the first and second waist belts 106 and 108 may overlap as shown in FIG. 1.

Referring to FIG. 25, as discussed above, in some exemplary configurations, the first and second discrete fastener components 186 and 188 may be bonded with the connection elements 202 at bonded regions 240 that are positioned along portions of the first and second discrete fastener components 186 and 188 that overlap the fastener elements 204.

Figure 26:
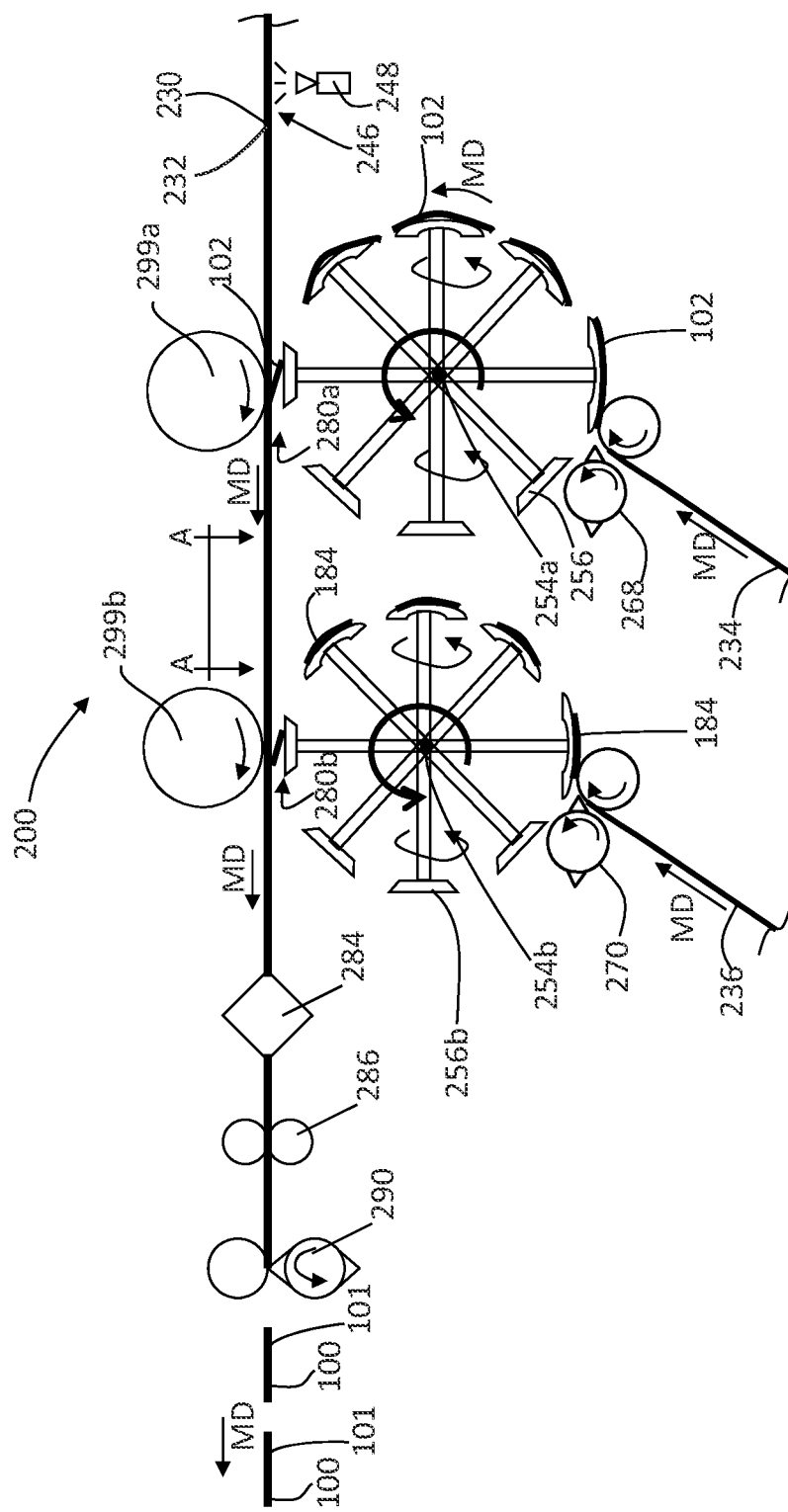
FIG. 26 is a schematic, side elevation view of a converting apparatus adapted to assemble pre-fastened refastenable absorbent articles.
Figure 27:
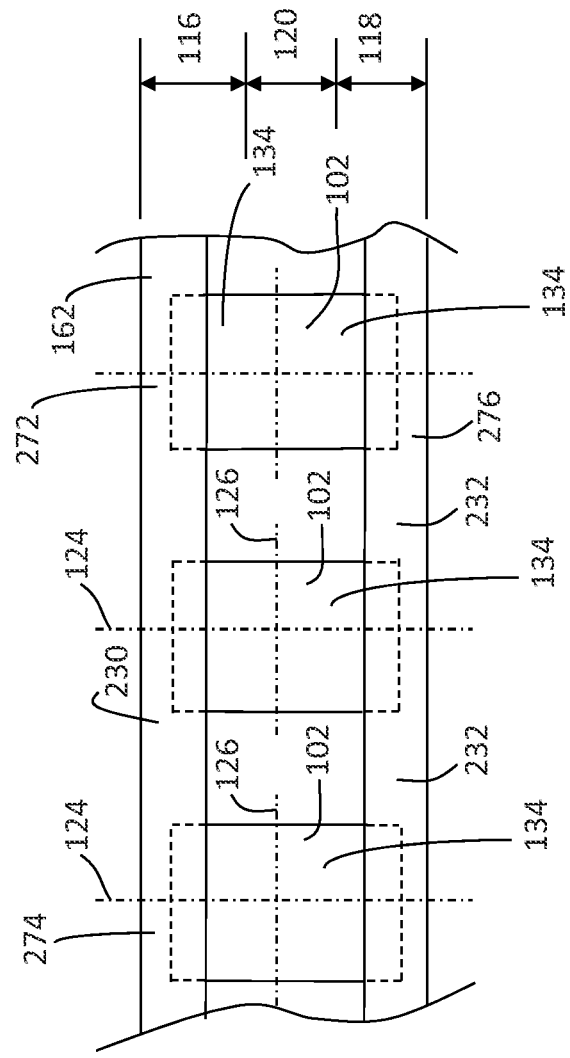
FIG. 27 is a continuous length of absorbent articles having discrete chassis intermittently spaced along continuous first and second belt substrates taken along line A-A of FIG. 26.

In another exemplary configuration, as shown in FIG. 26, the continuous length of chassis assemblies 234 may advance to a first carrier apparatus 250a and the continuous length of fastener assemblies 236 may advance to a second carrier apparatus 250b. For example, as shown in FIG. 27, a continuous length of chassis assemblies 234 may advance in the machine direction MD to the first carrier apparatus 250a and may be cut into discrete chassis 102 by a cutting member 268 positioned adjacent to the first carrier apparatus 250a. The first carrier apparatus 250a may be configured in various ways. Exemplary carrier apparatuses that may be used as the first carrier apparatus are described in U.S. patent application Ser. No. 13/447,531, filed on Apr. 16, 2012; U.S. patent application Ser. No. 13/447,544, filed on Apr. 16, 2012; U.S. patent application Ser. No. 13/447,568, filed on Apr. 16, 2012; and U.S. patent application Ser. No. 13/447,585, filed on Apr. 16, 2012. The first carrier apparatus 250a may operate similar to the carrier apparatus 250 described above with regard to FIG. 8. For example, the first carrier apparatus 250a may reorient the chassis 102 from the orientation shown in FIG. 15, wherein the longitudinal axis 124 is substantially parallel with the machine direction MD, to an orientation shown in FIG. 16, wherein the lateral axis 126 is substantially parallel with the machine direction MD.

Figure 17:
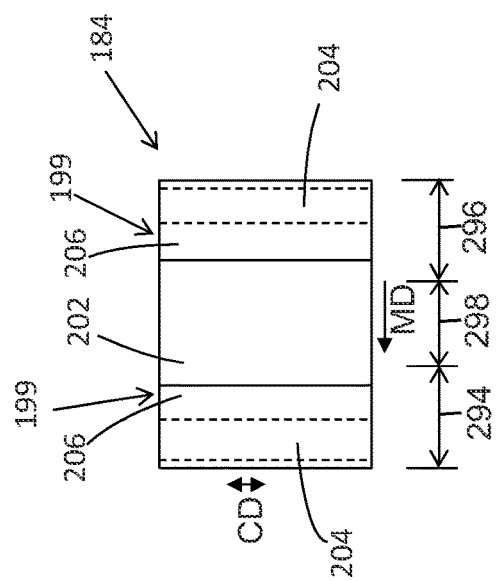
FIG. 17 is a schematic, plan view of a discrete fastener component.
Figure 16:
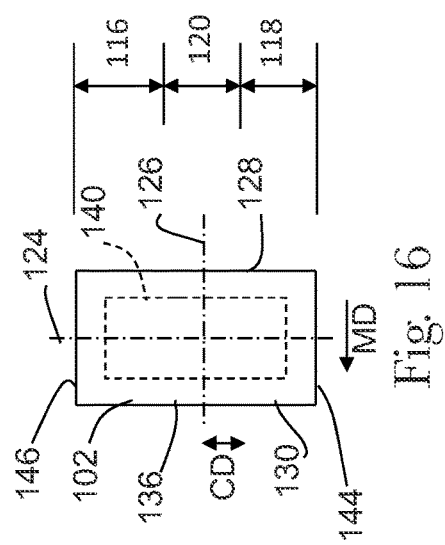
FIG. 16 is a schematic, plan view of a discrete chassis.

With reference to FIGS. 16, 17, and 26, the chassis 102 are transferred from the first carrier apparatus 250a and combined with advancing, continuous lengths of first and second waist belt webs 230 and 232 at a first nip 280a formed between the first carrier apparatus 250a and the first nip roll 299a. The first and second waist belt webs 230 and 232 each define an inner, wearer facing surface 272, 276 and an opposing outer, garment facing surface 274, 278. The inner, wearer facing surface 272 of the first waist belt web 230 may be combined with the outer, garment facing surface 134 of the chassis 102 along the first waist region 116 and the inner, wearer facing surface 276 of the second waist belt web 232 may be combined with the outer, garment facing surface 134 of the chassis 102 along the second waist region 118.

As shown in FIG. 26, adhesive 246 may be applied to the inner, wearer facing surfaces 272 and 276 of the first and second waist belt webs 230 and 232 before combining with the discrete chassis 102 at the first nip 280 formed between the first nip roll 299 and the carrier apparatus 250.

A continuous length of fastener assemblies 236 may advance in the machine direction MD to a second carrier apparatus 250b and may be cut into discrete fastener components 184 by the cutting member 270 positioned adjacent to the second carrier apparatus 250b. The first and second carrier apparatuses 250a and 250b may be configured the same, or may have different configurations. The second carrier apparatus 250b may operate similar to the carrier apparatus 250 described above with regard to FIG. 8. For example, the second carrier apparatus 250b may reorient the discrete fastener component 184 from the orientation shown in FIG. 13, wherein the first end region 294 of the discrete fastener component 184 is separated from the second end region 296 of the discrete fastener component 184 in the cross direction CD, to an orientation shown in FIG. 17, wherein the first end region 294 of the discrete fastener component 184 is separated from the second end region 296 of the discrete fastener component 184 in the machine direction MD. In some exemplary configurations, adhesive 246 may be applied to the second surface 199 of the discrete fastener components 184 using an adhesive applicator 248 while advancing on the second carrier apparatus 250b. In other exemplary configurations, the second surface 199 of the discrete fastener components 184 may be pre-glued prior to advancing onto the second carrier apparatus 250b.

Figure 18:
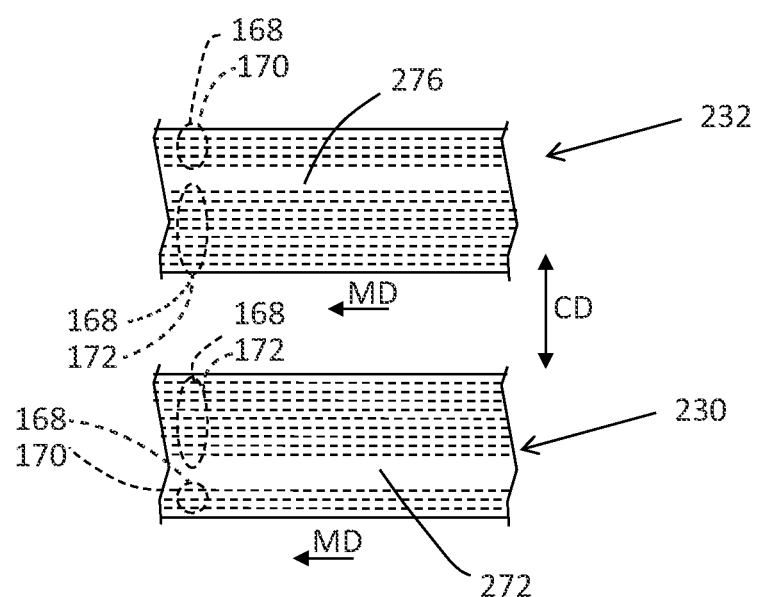
FIG. 18 is a schematic, plan view of continuous lengths of first and second waist belts taken along line F-F of FIG. 8.

With reference to FIGS. 18 and 26, the discrete fasteners 184 are transferred from the second carrier apparatus 250b and combined with the second waist belt web 232 at the second nip 280b formed between the second carrier apparatus 250b and a second nip roll 299b to form a continuous length of absorbent articles 282. The second surface 199 of the discrete fastener component 184 may be combined with the inner, wearer facing surface 276 of the second waist belt web 232 such that discrete chassis 102 are positioned adjacent to discrete fastener components 184 and discrete fastener components 184 are separated by discrete chassis 102.

The continuous length of absorbent articles 282 comprising discrete fastener components 184 may advance in a machine direction MD to a folding apparatus 284. At the folding apparatus 284, the chassis are folded along the lateral axis 126 to bring the first and second waist belt webs 230 and 232 into a facing relationship as shown in FIG. 19. Next, the continuous length of absorbent articles 284 is advanced to a bonding apparatus 286, wherein the fastener components 184 are joined with the first waist belt web 230 as shown in FIG. 21. The fastener components 184 may be connected with the first waist belt web 230 at bond regions 288 such as shown in FIG. 21. The continuous length of absorbent articles 284 are then advanced in the machine direction MD to a cutting member 290, wherein the first and second waist belt webs 230 and 232 are cut along the fastener component 184 to create discrete diapers 101 having first and second discrete fastener components 186 and 188, such as shown in FIGS. 1 and 24.

While the methods and apparatuses disclosed herein relate to assembling pre-fastened, refastenable pants, it is to be appreciated that the methods and apparatuses disclosed herein may be configured to assemble pants having permanent closure members. The methods and apparatuses disclosed herein may be used with the methods and apparatuses for forming pants having permanent closure members. Exemplary methods and apparatuses for forming pants having permanent closure members are described in, for example, U.S. patent application Ser. Nos. 13/447,531; 13/447,544; No. 13/447,568; and 13/447,585.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling refastenable absorbent articles, each absorbent article comprises a chassis having a topsheet, backsheet, and an absorbent core disposed between the topsheet and the backsheet, wherein the chassis defines a first waist region longitudinally opposed to a second waist region, and having a longitudinal axis and a lateral axis, each absorbent article further comprising a first waist belt connected with the first waist region and a second waist belt connected with the second waist region, wherein a first discrete fastener component joins first end regions of the first and second waist belts and a second discrete fastener component joins second end regions of the first and second waist belts, the method comprising the steps of:

advancing a continuous length of chassis assemblies in a machine direction;

cutting the continuous length of chassis assemblies into discrete chassis;

advancing the discrete chassis in the machine direction onto a carrier apparatus, wherein the carrier apparatus comprises a frame rotatable about an axis of rotation, and a transfer member connected with the frame, wherein the transfer member is rotatable about a second axis of rotation that is orthogonal to the first axis of rotation, wherein the transfer member has a first portion and a second portion, wherein the topsheet of the discrete chassis contacts the first portion of the transfer member;

advancing a continuous length of fastener assemblies in the machine direction;

cutting the continuous length of fastener assemblies into discrete fastener components, wherein each discrete fastener component define a first surface and a second surface, each discrete fastener component comprising a first end region and an opposing second end region separated by a central region; and advancing the discrete fastener components in the machine direction onto the carrier apparatus, wherein the second surface of the discrete fastener component contacts the second portion of the transfer member, wherein the discrete fastener component is positioned adjacent to the chassis.

2. A method for assembling refastenable absorbent articles, each absorbent article comprises a chassis having a topsheet, backsheet, and an absorbent core disposed between the topsheet and the backsheet, wherein the chassis defines a first waist region longitudinally opposed to a second waist region, and having a longitudinal axis and a lateral axis, each absorbent article further comprising a first waist belt connected with the first waist region and a second waist belt connected with the second waist region, wherein a first discrete fastener component joins first end regions of the first and second waist belts and a second discrete fastener component joins second end regions of the first and second waist belts, wherein the first and second discrete fastener components are refastenably connected with the first waist belt and permanently connected with the second waist belt, the method comprising the steps of:

advancing a continuous length of chassis assemblies in a machine direction;

cutting the continuous length of chassis assemblies into discrete chassis;

advancing the discrete chassis in the machine direction onto a carrier apparatus, wherein the carrier apparatus comprises a frame rotatable about an axis of rotation, and a transfer member connected with the frame, wherein the transfer member is rotatable about a second axis of rotation that is orthogonal to the first axis of rotation, wherein the transfer member has a first portion and a second portion, wherein the topsheet of the discrete chassis contacts the first portion of the transfer member;

advancing a continuous length of fastener assemblies in the machine direction;

cutting the continuous length of fastener assemblies into discrete fastener components, wherein each discrete fastener component define a first surface and a second surface, each discrete fastener component comprising a first end region and an opposing second end region separated by a central region;

advancing the discrete fastener components in the machine direction onto the carrier apparatus, wherein the second surface of the discrete fastener component contacts the second portion of the transfer member, wherein the discrete fastener component is positioned adjacent to the chassis;

advancing a first waist belt web in the machine direction, wherein the first waist belt web defines a first surface and a second surface;

advancing a second waist belt web in the machine direction, wherein the second waist belt web defines a first surface and a second surface;

reorienting the discrete chassis such that the lateral axis is parallel with the machine direction by rotating the transfer member about the second axis of rotation;

combining the first waist region of the chassis intermittently along the first surface of the first waist belt web, the second waist region of the chassis intermittently along the first surface of the second waist belt;

combining the first surface of the discrete fastener component to the first surface of the second waist belt web;

folding the chassis to position the first waist region of the chassis into a face-to-face relationship with the second waist region of the chassis using a folding apparatus, wherein the second surface of the discrete fastener component is in a face-to-face relationship with the folding apparatus;

bonding the second surface of the discrete fastener component with the first waist belt web; and cutting the first and second waist belt webs in a cross direction along the central region of the discrete fastener component to form a first absorbent article having a first discrete fastener component and a second absorbent article having a second discrete fastener component.

3. The method of claim 2, wherein the step of bonding the second surface of the discrete fastener component with the first waist belt web further comprises directing hot air toward the second surface of the first waist belt web.

4. The method of claim 2, wherein each discrete fastener component further comprises a connection element connected with a first surface of the first and second fastener elements, and a side panel connected with a second surface of each of the first and second fastener elements.

5. The method of claim 4, wherein the first surface of the discrete fastener component comprises the connection element, and the second surface of the discrete fastener component comprises the side panels.

6. The method of claim 2, wherein the first discrete fastener component comprises a first fastener element, and the second discrete fastener component comprises a second fastener element.

7. The method of claim 6, wherein the first and second fastener elements are selected from the group consisting of: hook and loop fasteners, buttons, snaps, tab and slot fasteners, tape fasteners, adhesive fasteners, cohesive fasteners, magnetic fasteners, hermaphroditic fasteners, and combinations thereof.

8. The method of claim 2, wherein the first surface of the first and second waist belt webs is an inner, wearer facing surface and the second surface of the first and second waist belt webs is an outer, garment facing surface.

9. The method of claim 2, wherein the first waist belt is a front waist belt and the second waist belt is a back waist belt.

10. A method for assembling refastenable absorbent articles, each absorbent article comprises a chassis having a topsheet, backsheet, and an absorbent core disposed between the topsheet and the backsheet, wherein the chassis defines a first waist region longitudinally opposed to a second waist region, and having a longitudinal axis and a lateral axis, each absorbent article further comprising a first waist belt connected with the first waist region and a second waist belt connected with the second waist region, wherein a first discrete fastener component joins first end regions of the first and second waist belts and a second discrete fastener component joins second end regions of the first and second waist belts, wherein the first and second discrete fastener components are refastenably connected with the first waist belt and permanently connected with the second waist belt, the method comprising the steps of:

advancing a continuous length of chassis assemblies in a machine direction;

cutting the continuous length of chassis assemblies into discrete chassis;

advancing the discrete chassis in the machine direction onto a carrier apparatus, wherein the carrier apparatus comprises a frame rotatable about an axis of rotation, and a transfer member connected with the frame, wherein the transfer member is rotatable about a second axis of rotation that is orthogonal to the first axis of rotation, wherein the transfer member has a first portion and a second portion, wherein the topsheet of the discrete chassis contacts the first portion of the transfer member;

advancing a continuous length of fastener assemblies in the machine direction;

cutting the continuous length of fastener assemblies into discrete fastener components, wherein each discrete fastener component define a first surface and a second surface, each discrete fastener component comprising a first end region and an opposing second end region separated by a central region;

advancing the discrete fastener components in the machine direction onto the carrier apparatus, wherein the second surface of the discrete fastener component contacts the second portion of the transfer member, wherein the discrete fastener component is positioned adjacent to the chassis;

advancing a first waist belt web in the machine direction, wherein the first waist belt web defines a first surface and a second surface;

advancing a second waist belt web in the machine direction, wherein the second waist belt web defines a first surface and a second surface;

reorienting the discrete chassis such that the lateral axis is parallel with the machine direction by rotating the transfer member about the second axis of rotation;

combining the first waist region of the chassis intermittently along the first surface of the first waist belt web, the second waist region of the chassis intermittently along the first surface of the second waist belt;

combining the first surface of the discrete fastener component to the first surface of the second waist belt web;

folding the chassis to position the first waist region of the chassis into a face-to-face relationship with the second waist region of the chassis using a folding apparatus, wherein the second surface of the discrete fastener component is in a face-to-face relationship with the folding apparatus;

connecting the second surface of the discrete fastener component with the first waist belt web; and cutting the first and second waist belt webs in a cross direction along the central region of the discrete fastener component to form a first absorbent article having a first discrete fastener component and a second absorbent article having a second discrete fastener component.

11. The method of claim 10, wherein each discrete fastener component further comprises a connection element connected with a first surface of the first and second fastener elements, and a side panel connected with a second surface of each of the first and second fastener elements.

12. The method of claim 10, wherein the first discrete fastener component comprises a first fastener element, and the second discrete fastener component comprises a second fastener element.

13. The method of claim 12, wherein the first and second fastener elements are selected from the group consisting of: hook and loop fasteners, buttons, snaps, tab and slot fasteners, tape fasteners, adhesive fasteners, cohesive fasteners, magnetic fasteners, hermaphroditic fasteners, and combinations thereof.

14. The method of claim 10, wherein the first surface of the first and second waist belt webs is an inner, wearer facing surface and the second surface of the first and second waist belt webs is an outer, garment facing surface.

15. The method of claim 10, wherein the first waist belt is a front waist belt and the second waist belt is a back waist belt.

\* \* \* \* \*